(12) United States Patent
Mukai et al.

(10) Patent No.: US 8,361,047 B2
(45) Date of Patent: Jan. 29, 2013

(54) ABSORBENT ARTICLE HAVING SPACED NARROW WIDTH SECTIONS

(75) Inventors: Hirotomo Mukai, Kagawa (JP); Akiyoshi Kinoshita, Kagawa (JP); Tomoko Tsuji, Kagawa (JP); Norihiko Ishikawa, Kanonji (JP); Tatsuya Hashimoto, Kagawa (JP)

(73) Assignee: Uni-Charm Corporation, Shikokuchuo-shi (JP)

( * ) Notice: Subject to any disclaimer, the term of this patent is extended or adjusted under 35 U.S.C. 154(b) by 1057 days.

(21) Appl. No.: 11/952,258

(22) Filed: Dec. 7, 2007

(65) Prior Publication Data

US 2008/0140042 A1 Jun. 12, 2008

(30) Foreign Application Priority Data

Dec. 7, 2006 (JP) ................................. 2006-331240

(51) Int. Cl.
*A61F 13/494* (2006.01)
*A61F 13/496* (2006.01)

(52) U.S. Cl. .............................. 604/385.27; 604/385.25

(58) Field of Classification Search ........... 604/385.101, 604/385.23, 385.24, 385.01, 385.25, 385.21, 604/385.22, 385.28, 385.27
See application file for complete search history.

(56) References Cited

U.S. PATENT DOCUMENTS 2,062,594 A * 12/1936 McNair .................... 604/385.24
3,192,927 A * 7/1965 Chauviere .................... 604/381
3,441,023 A    4/1969 Rijssenbeek
4,323,070 A * 4/1982 Ternstrom et al. ........ 604/385.25
4,336,803 A * 6/1982 Repke ...................... 604/385.25
4,582,550 A * 4/1986 Sigl ................................. 156/84
4,640,859 A * 2/1987 Hansen et al. ................. 428/105
4,655,760 A    4/1987 Morman et al.
4,775,375 A * 10/1988 Aledo ........................... 604/378
4,808,177 A    2/1989 DesMarais et al.

(Continued)

FOREIGN PATENT DOCUMENTS

JP         7-447       1/1995
JP    2003-10244       1/2003

(Continued)

OTHER PUBLICATIONS

Notice of Reasons for Rejection mailed Jul. 17, 2012, directed to Japanese Application No. 2008-548337; 3 pages.

(Continued)

*Primary Examiner* — Jackie Ho
*Assistant Examiner* — Paula Craig
(74) *Attorney, Agent, or Firm* — Morrison & Foerster LLP

(57) ABSTRACT

The absorbent article includes a chassis, a crotch region, an absorbent body, and an elastic member arranged along a side edge in width direction of the crotch region. The oblong absorbent body arranged in the crotch region includes a first narrow width section, a second narrow width section, a center low rigidity section formed along a center line that halves the absorbent article in the width direction and a pair of lateral low rigidity sections provided at both sides of the center low rigidity section in the width direction with a substantially equal interval. Skin contacting face-side sheets and non-skin contacting face-side sheets 6 and 10 are arranged in the crotch region. The initial tensile strength of the skin contacting face-side sheets is lower than that of the non-skin contacting face-side sheets or that of the chassis 2.

5 Claims, 13 Drawing Sheets

U.S. PATENT DOCUMENTS

| | | | |
|---|---|---|---|
| 4,834,736 A * | 5/1989 | Boland et al. | 604/385.22 |
| 4,906,243 A * | 3/1990 | Dravland | 604/394 |
| RE33,351 E | 9/1990 | Papajohn | |
| 5,167,653 A | 12/1992 | Igaue et al. | |
| 5,171,302 A * | 12/1992 | Buell | 604/385.23 |
| 5,342,343 A | 8/1994 | Kitaoka et al. | |
| 5,366,452 A * | 11/1994 | Widlund et al. | 604/385.24 |
| 5,451,219 A | 9/1995 | Suzuki et al. | |
| 5,476,458 A | 12/1995 | Glaug et al. | |
| 5,527,300 A | 6/1996 | Sauer | |
| H1630 H | 1/1997 | Roe et al. | |
| 5,591,150 A * | 1/1997 | Olsen et al. | 604/385.23 |
| 5,643,242 A * | 7/1997 | Lavon et al. | 604/385.21 |
| 5,643,243 A * | 7/1997 | Klemp | 604/385.28 |
| 5,662,634 A | 9/1997 | Yamamoto et al. | |
| 5,702,378 A * | 12/1997 | Widlund et al. | 604/373 |
| 5,895,380 A | 4/1999 | Turi et al. | |
| 5,928,211 A * | 7/1999 | Gustafsson et al. | 604/385.22 |
| 5,941,863 A * | 8/1999 | Guidotti et al. | 604/378 |
| 6,099,515 A * | 8/2000 | Sugito | 604/385.01 |
| 6,210,387 B1 * | 4/2001 | Rudberg et al. | 604/385.27 |
| 6,222,092 B1 | 4/2001 | Hansen et al. | |
| 6,293,933 B1 * | 9/2001 | Ahlstrand | 604/385.101 |
| 6,326,525 B1 * | 12/2001 | Hamajima et al. | 604/378 |
| 6,350,258 B1 * | 2/2002 | Markowiecki | 604/385.201 |
| 6,375,644 B2 | 4/2002 | Mizutani | |
| 6,436,081 B1 | 8/2002 | Wada et al. | |
| 6,475,199 B1 * | 11/2002 | Gann et al. | 604/385.01 |
| 6,475,203 B1 | 11/2002 | Rubio | |
| 6,503,238 B1 * | 1/2003 | Torstensson et al. | 604/385.28 |
| 6,569,137 B2 | 5/2003 | Suzuki et al. | |
| 6,602,234 B2 | 8/2003 | Klemp et al. | |
| 6,617,490 B1 * | 9/2003 | Chen et al. | 604/380 |
| 6,648,865 B1 | 11/2003 | Stiehl et al. | |
| 6,648,869 B1 | 11/2003 | Gillies et al. | |
| 6,652,503 B1 * | 11/2003 | Bradley | 604/385.17 |
| 6,682,515 B1 | 1/2004 | Mizutani et al. | |
| 6,852,101 B2 * | 2/2005 | Damaghi et al. | 604/385.101 |
| 7,087,044 B2 * | 8/2006 | Ohnishi | 604/385.01 |
| 7,105,716 B2 | 9/2006 | Baratian et al. | |
| 7,135,014 B2 | 11/2006 | Sasaki et al. | |
| 7,722,590 B2 * | 5/2010 | Tsuji et al. | 604/385.28 |
| 8,211,815 B2 | 7/2012 | Baker et al. | |
| 2002/0013563 A1 * | 1/2002 | Lassen et al. | 604/385.01 |
| 2002/0029029 A1 * | 3/2002 | Otsubo | 604/385.101 |
| 2002/0151861 A1 | 10/2002 | Klemp et al. | |
| 2003/0083631 A1 * | 5/2003 | Chen et al. | 604/380 |
| 2003/0083632 A1 * | 5/2003 | Rubio | 604/385.01 |
| 2003/0135177 A1 | 7/2003 | Baker | |
| 2004/0193127 A1 | 9/2004 | Hansson et al. | |
| 2004/0243081 A1 * | 12/2004 | Suzuki et al. | 604/378 |
| 2005/0055000 A1 * | 3/2005 | Ohnishi | 604/367 |
| 2005/0124952 A1 * | 6/2005 | Zehner et al. | 604/385.01 |
| 2005/0124953 A1 * | 6/2005 | Woltman et al. | 604/385.01 |
| 2006/0069371 A1 * | 3/2006 | Ohashi et al. | 604/385.01 |
| 2006/0135933 A1 * | 6/2006 | Newlin et al. | 604/385.22 |
| 2006/0264859 A1 * | 11/2006 | Tsuji et al. | 604/385.28 |
| 2007/0078422 A1 * | 4/2007 | Glaug et al. | 604/380 |
| 2008/0139067 A1 * | 6/2008 | Mukai et al. | 442/328 |
| 2008/0140038 A1 * | 6/2008 | Sasayama et al. | 604/367 |
| 2008/0140042 A1 | 6/2008 | Mukai et al. | |
| 2010/0324521 A1 | 12/2010 | Mukai et al. | |
| 2010/0324523 A1 | 12/2010 | Mukai et al. | |

FOREIGN PATENT DOCUMENTS

| | | |
|---|---|---|
| JP | 2004041311 | 2/2004 |
| JP | 2006507077 | 3/2006 |
| JP | 2006095156 | 4/2006 |
| JP | 2007330543 | 12/2007 |

OTHER PUBLICATIONS

Mukai et al., U.S. Office Action mailed May 2, 2012, directed to U.S. Appl. No. 12/850,225; 12 pages.

Mukai et al., U.S. Office Action mailed May 25, 2012, directed to U.S. Appl. No. 12/850,309; 9 pages.

Mukai et al., U.S. Office Action mailed Oct. 12, 2012, directed to U.S. Appl. No. 12/850,225; 11 pages.

Mukai et al., U.S. Office Action mailed Oct. 12, 2012, directed to U.S. Appl. No. 12/850,309; 13 pages.

* cited by examiner

90mm

30mm

130mm

ABSORBENT ARTICLE HAVING SPACED NARROW WIDTH SECTIONS

This application is based on and claims the benefit of priority from Japanese Patent Application No. 2006-331240, filed on Dec. 7, 2006, the content of which is incorporated herein by reference.

BACKGROUND OF THE INVENTION

1. Field of the Invention

The present invention relates to an absorbent article such as a disposable diaper.

2. Related Art

Conventionally, a disposable diaper has been known as an absorbent article that absorbs and retains excretory substance (urine, stool) discharged from a human body. The absorbent article includes, for example, a top liquid-permeable sheet, a back liquid-impermeable sheet, and liquid-retentive absorbent body provided between the top sheet and the back sheet. The disposable diaper as described above functions so that, when being worn by a user, excretory substance (e.g., urine) discharged from the user is absorbed via the top liquid-permeable sheet and retained by the absorbent body and excretory substance is prevented by the back liquid-impermeable sheet from leaking to the exterior of the absorbent article.

Disposable diapers have been designed in many ways with a purpose of preventing the leakage or retention of excretory substance (e.g., stool). For example, a diaper has been provided in which a top face and a back face of an absorption layer includes grooves along the longitudinal direction of the absorption layer (see Japanese Patent No. 3616077, hereinafter referred to as "Patent Publication 1"). This groove along the longitudinal direction disperses excretory substance in the longitudinal direction.

Generally, excretory liquid such as urine is discharged to a center section in the longitudinal direction of the absorbent body. According to the diaper of Patent Publication 1, excretory liquid is guided by the groove formed along the longitudinal direction.

Patent Publication 1 describes a groove for guiding excretory liquid to absorbent body. However, Patent Publication 1 does not disclose at all that a part of an absorbent body is deformed so as to be abutted with an excretory part having a urethral meatus or anus. Patent Publication 1 also does not disclose at all that a side edge of absorbent body is bent toward legs to suppress the leakage of excretory liquid.

SUMMARY OF THE INVENTION

It is an objective of the present invention to provide an absorbent article that is abutted to an excretory part of a human body when being worn by a user and that is deformed to suppress the leakage of excretory substance.

The present inventors have completed the present invention by discovering that a function for preventing the leakage of excretory liquid, such as urine, and absorption capability can be improved by providing an absorbent body structured by a low rigidity section at a crotch region of an oblong diaper at which the absorbent body is bent and that is formed along a center line for halving the absorbent body to two parts in the width direction and a pair of lateral low rigidity sections that are provided at both sides in the width direction of the center low rigidity section with a substantially equal interval so that the both sides edges in the width direction of the absorbent body have gathers for preventing the leakage.

According to a first aspect of the present invention, an absorbent article having a width and a length orthogonal to the width, including: a chassis having at least a front torso surrounding region and a rear torso surrounding region arranged along a longitudinal direction of the absorbent article; a crotch region provided between the front torso surrounding region and the rear torso surrounding region of the chassis; an oblong absorbent body extending from the front torso surrounding region to the rear torso surrounding region along the longitudinal direction; a torso opening section formed at one side when in a wearing mode; a pair of leg openings formed at another side when in the wearing mode; a skin-contacting face facing an inner face when in the wearing mode; a not-skin-contacting face facing an outer face when in the wearing mode; and an elastic member arranged along a side edge in the width direction of the crotch region constituting the leg opening, in which the absorbent body includes: a first narrow width section; a second narrow width section arranged longitudinally spaced from the first narrow width section; a center low rigidity section formed along a center line that halves the absorbent article in the width direction; and a pair of lateral low rigidity sections provided at both sides of the center low rigidity section in the width direction with a substantially equal interval; in which the crotch region is structured so that the skin-contacting face of the absorbent body has a skin contacting face-side sheet and the not-skin-contacting face has either one of a not-skin contacting face-side sheet and the chassis, and in which the skin contacting face-side sheet has, while in a stretched state, a lower initial tensile strength in the width direction than that of either one of the not-skin contacting face-side sheet and the chassis.

According to a second aspect of the present invention, an absorbent article having a width and a length orthogonal to the width, including: a chassis having at least a front torso surrounding region and a rear torso surrounding region arranged along a longitudinal direction of the absorbent article; a crotch region positioned between the front torso surrounding region and the rear torso surrounding region in the chassis; an oblong absorbent body provided extending from the front torso surrounding region to the rear torso surrounding region along the longitudinal direction; a torso opening section formed at one side when in a wearing mode; a pair of leg openings formed at another side when in the wearing mode; a skin-contacting face facing an inner face when in the wearing mode; a not-skin-contacting face facing an outer face when in the wearing mode; and an elastic member arranged along a side edge in the width direction of the crotch region constituting the leg opening absorbent body, in which the absorbent body includes: a first narrow width section; a second narrow width section arranged longitudinally spaced from the first narrow width section; a center low rigidity section formed along a center line that halves the absorbent article in the width direction; and a pair of lateral low rigidity sections provided at both sides of the center low rigidity section in the width direction with a substantially equal interval; in which the crotch region is structured so that the skin-contacting face of the absorbent body has a skin contacting face-side sheet and the not-skin-contacting face has either one of the not-skin contacting face-side sheet and the chassis, and in which the length in the width direction of the skin contacting face-side sheet is longer than that of the absorbent body.

In a third aspect of the absorbent article as described in the first or second aspect of the present invention, the absorbent body further includes a center absorbing section provided in the longitudinal direction between the first narrow width section and the second narrow width section, and the center absorbing section is shaped so that both edges in the width direction protrude more than the first narrow width section and the second narrow width section protrude to outer sides of the width direction, respectively.

In a fourth aspect of the absorbent article as described in the third aspect of the present invention, in which both side edges at outer sides in the width direction of the absorbent body have a pair of stretching sheets arranged along the longitudinal direction, and the respective stretching sheets are arranged to extend over both ends of the center absorbing section in the longitudinal direction to outer sides in the longitudinal direction and are arranged to extend over both ends in the width direction of the center absorbing section to outer sides in the width direction.

In a fifth aspect of the absorbent article as described in the fourth aspect of the present invention, further includes: a pair of side regions arranged widthwise outside each of the a pair of lateral low rigidity sections; and a pair of center regions arranged between the center low rigidity section and each of the pair of lateral low rigidity sections, the stretching sheet is provided to be superposed on the side region in the width direction.

According to a sixth aspect of the absorbent article as described in the fifth aspect of the present invention, in which in the wearing condition of the absorbent article, the side region is bent so that an end of an outer side in the width direction of the side region is raised in the thickness direction of the absorbent body, and the center region is bent so that an end of an inner side in the width direction of the center region is raised in the thickness direction, the absorbent body is consequently deformed to have a W-letter shaped cross section in the width direction of the center absorbing section.

According to a seventh aspect of the present invention, an absorbent body used for an absorbent article is provided including: a first narrow width section; a second narrow width section arranged longitudinally spaced from the first narrow width section of the absorbent article; a center absorbing section arranged between the first narrow width section and the second narrow width section in the longitudinal direction; a center low rigidity section that is formed along a center line that halves the absorbent body in the width direction; and lateral low rigidity sections provided at both sides of the center low rigidity section in the width direction with a substantially equal interval; in which the first narrow width section and the second narrow width section have therebetween, in the longitudinal direction, the center absorbing section shaped so that both edges in the width direction protrude to outer sides in the width direction and become wider than the first narrow width section and the second narrow width section.

Thus, the present invention can provide an absorbent article with an absorbent body which is brought into contact with excretory part of the body during wearing and which deforms to inhibit a leakage of discharged matter.

DETAILED DESCRIPTION OF THE INVENTION

Hereinafter, embodiments of the present invention will be described with reference to the drawings. It is noted that embodiments of the present invention are not limited to the following embodiments and the technical scope of the present invention is not limited to these embodiments.

In this specification, it is assumed that an inner face of a disposable diaper 1 facing a body of a user is a skin-contacting face and an outer face opposite to the skin-contacting face is a not-skin-contacting face. This skin-contacting face is a top face at which a top sheet is provided. The not-skin-contacting face is a back face. In this specification, the center line halving an absorbent body in the longitudinal direction in a developed diaper is assumed as an inner side and a width direction orthogonal to this longitudinal direction that is away from the center and at which a diaper edge is arranged is assumed as an outer side.

In this embodiment, a pants-type disposable diaper will be mainly described in which a front torso surrounding region and a rear torso surrounding region are joined at a predetermined joint section to form a torso opening and a pair of leg openings. However, the present invention is not limited to this type of disposable diaper. For example, the invention also may be applied to a development-type disposable diaper that can be worn by a used by attaching a front torso surrounding region with a rear torso surrounding region by an attaching member or the like. For example, the invention also may be applied to a pants-type disposable diaper in which predetermined joint sections of a front torso surrounding region and a rear torso surrounding region of a pants-type disposable diaper are attached by a re-attachable attaching member (e.g., hook and loop fastener) as used in a development-type disposable diaper so that the pants-type disposable diaper can be unattached despite the pants-type structure and the pants-type disposable diaper can be developed and reattached.

In this embodiment, the term "wearing stage" means a status in which an absorbent article can be worn by a user or a period just after the absorbent article is worn by a user. For example, in the case of a pants-type diaper, the term "wearing stage" means that predetermined positions are joined and the diaper is worn by a user to provide a pants-like shape (so-called wearing mode). The term "wearing condition" means a condition after the diaper is worn by a user.

Figure 1:
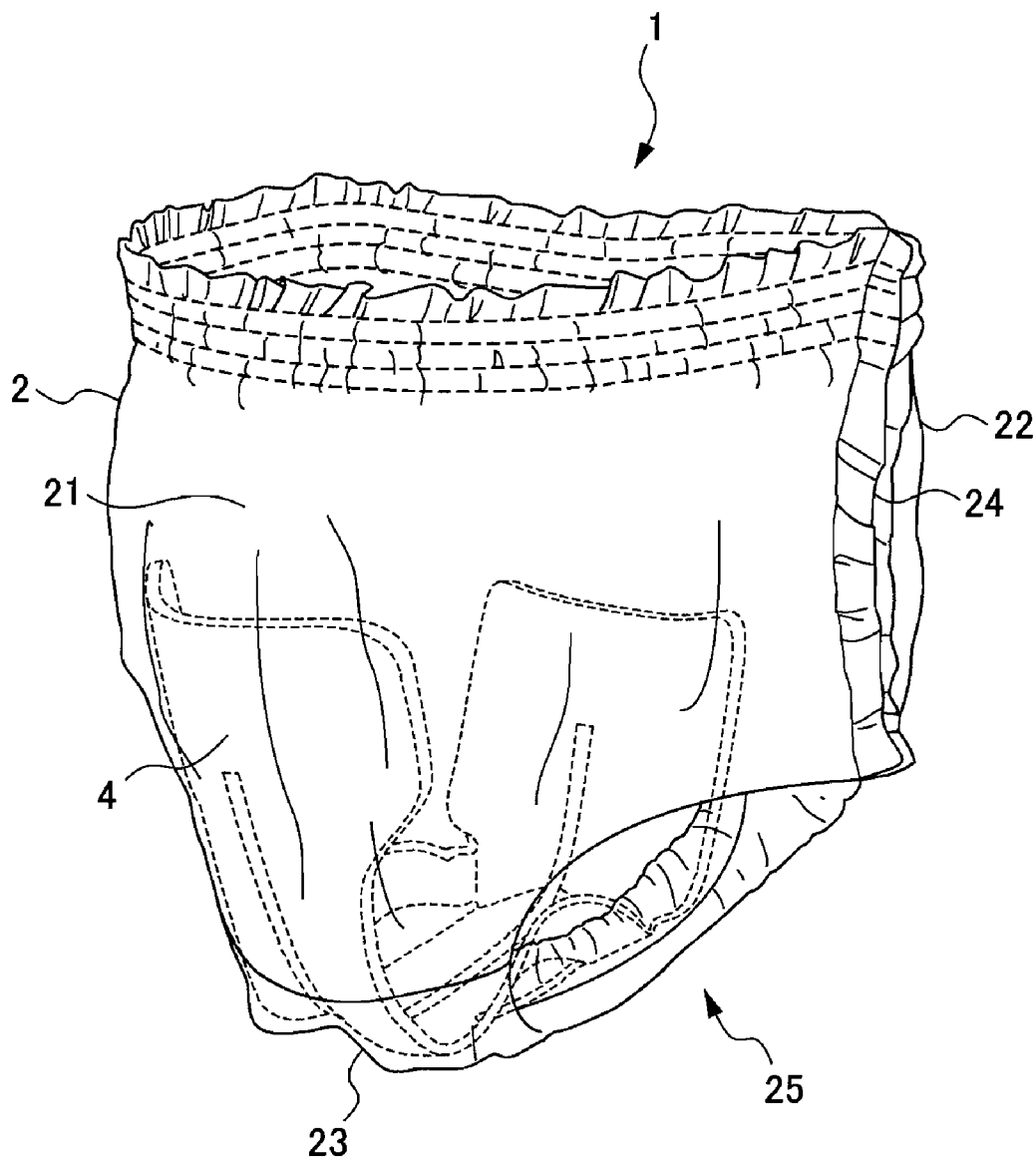
FIG. 1 is a perspective view showing a disposable diaper of the present invention.
Figure 2:
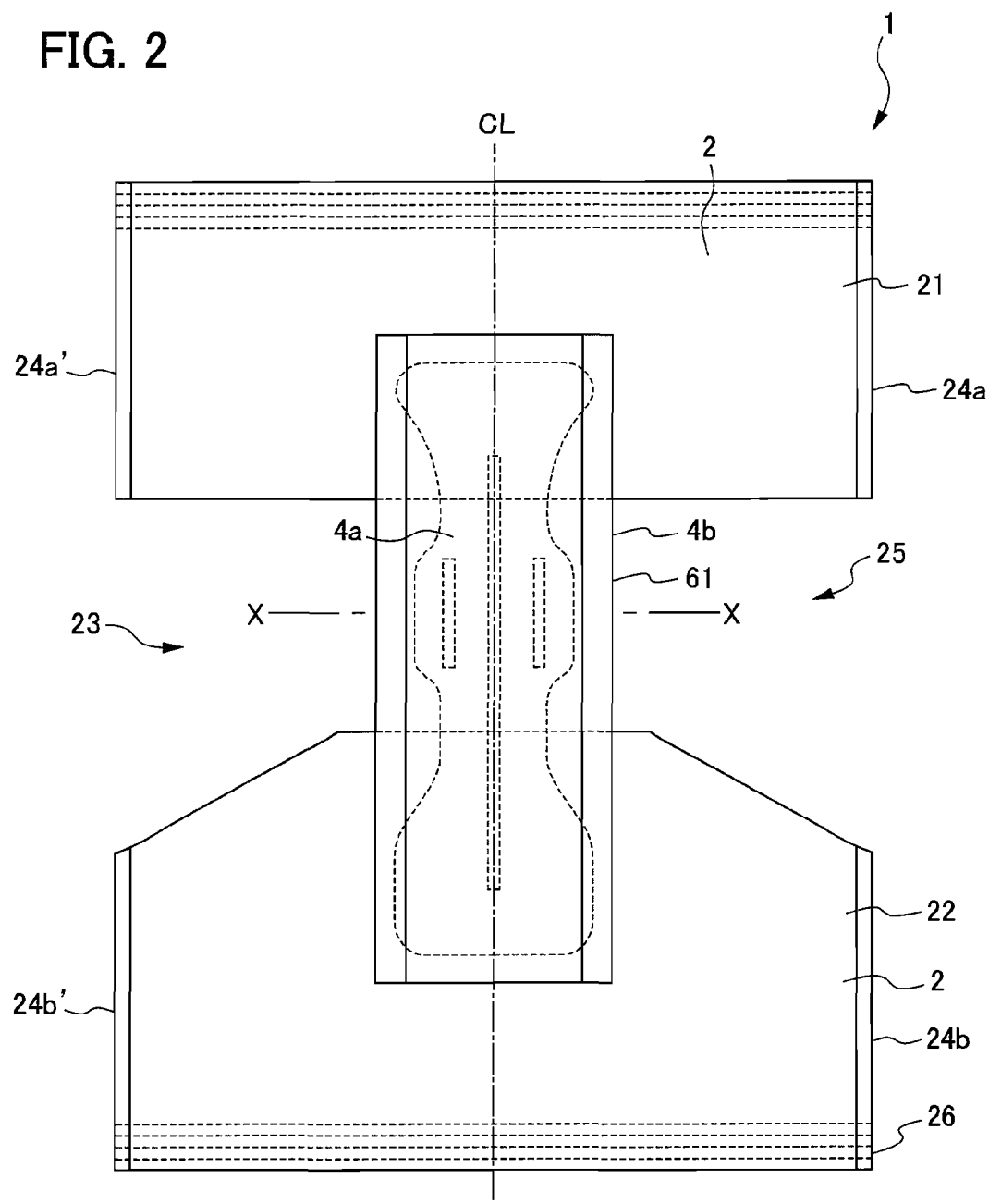
FIG. 2 is a development view illustrating a developed disposable diaper according to an embodiment of the present invention.
Figure 3:
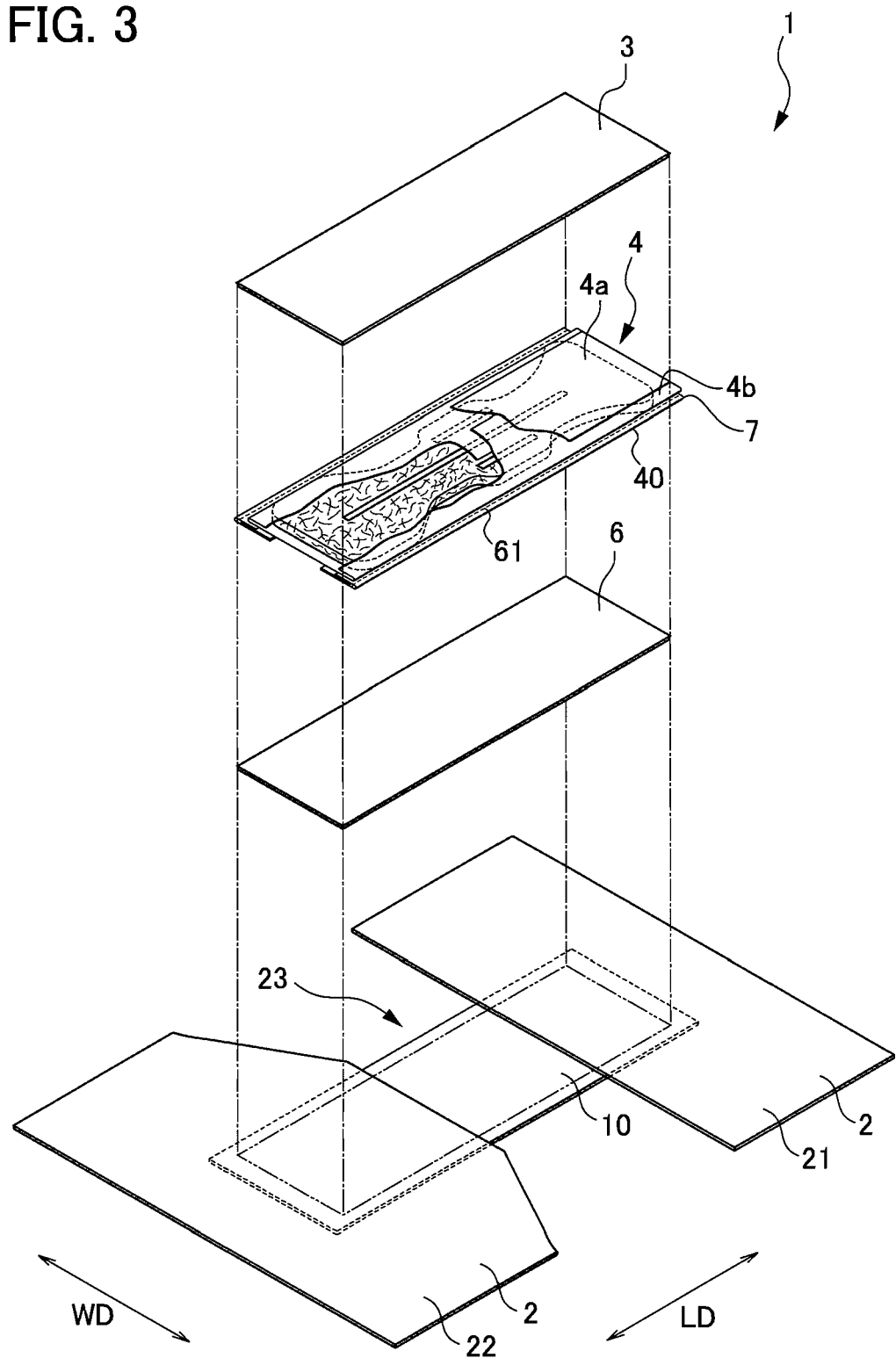
FIG. 3 is an exploded view illustrating the disposable diaper according to an embodiment of the present invention.
Figure 4A:
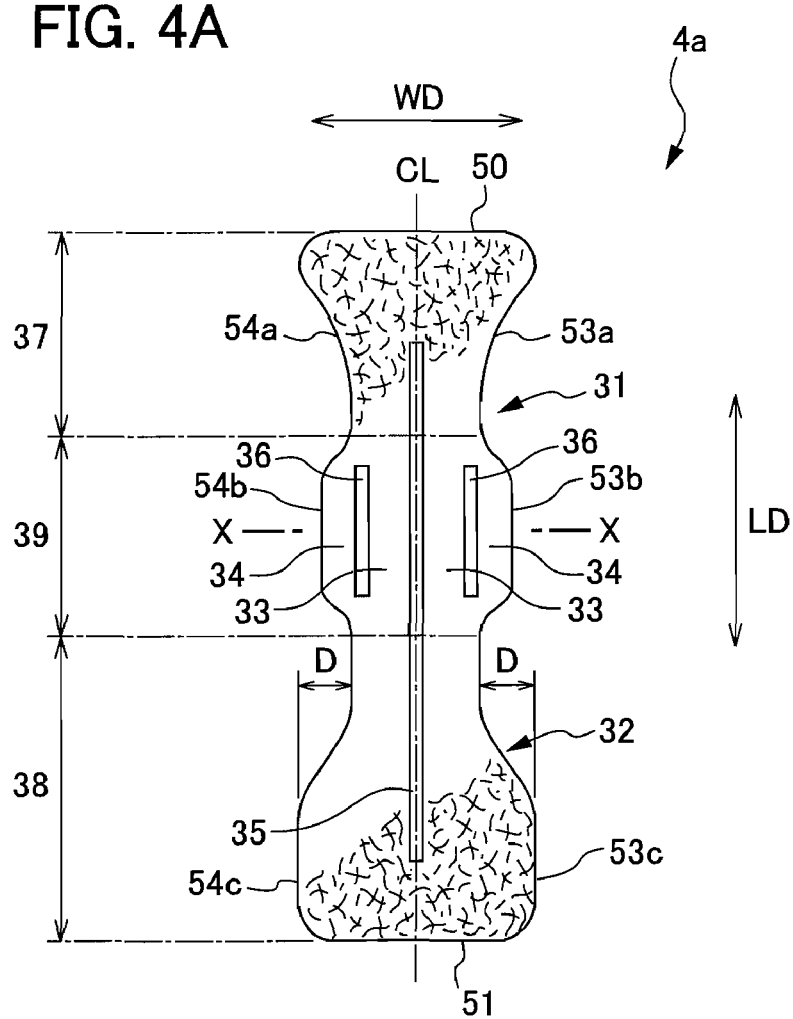
FIG. 4A is a front view illustrating an absorbent body of the disposable diaper according to an embodiment of the present invention.
Figure 4B:
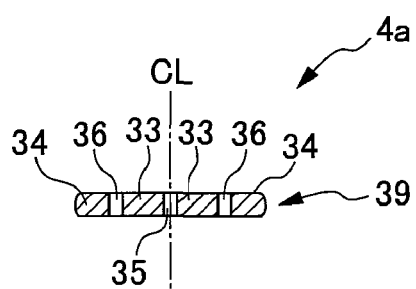
FIG. 4B is a cross-sectional view taken along X-X in FIG. 4A.
Figure 5:
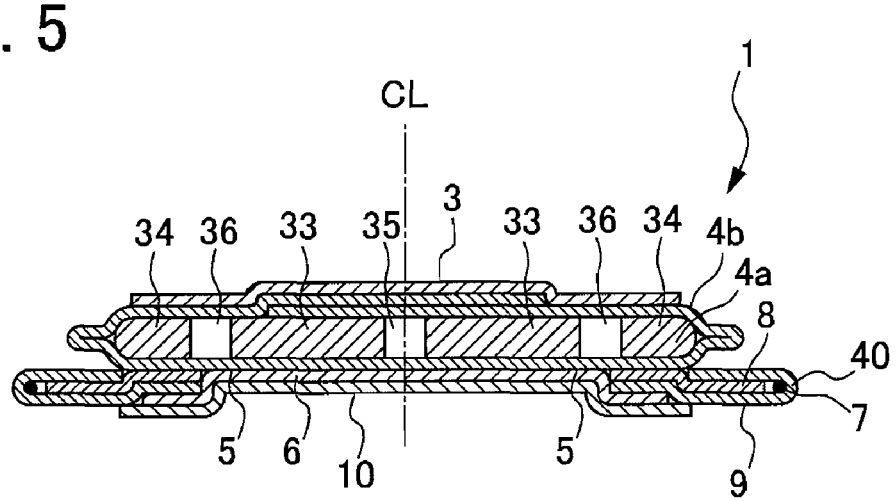
FIG. 5 is a cross-sectional view taken along X-X in FIG. 2.
Figure 6:
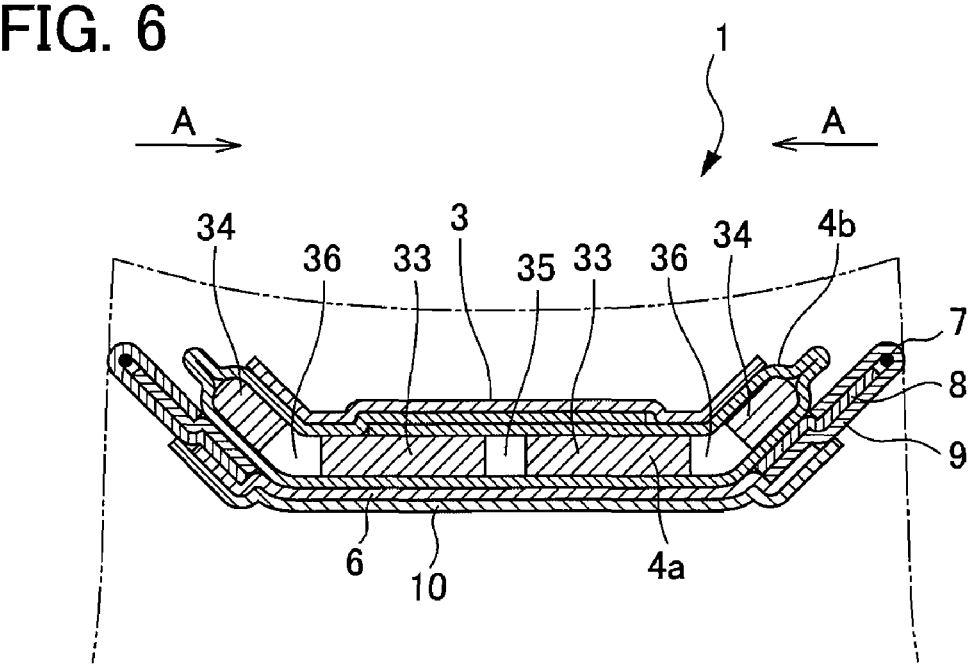
FIG. 6 illustrates that the disposable diaper according to the present embodiment is deformed.
Figure 7:
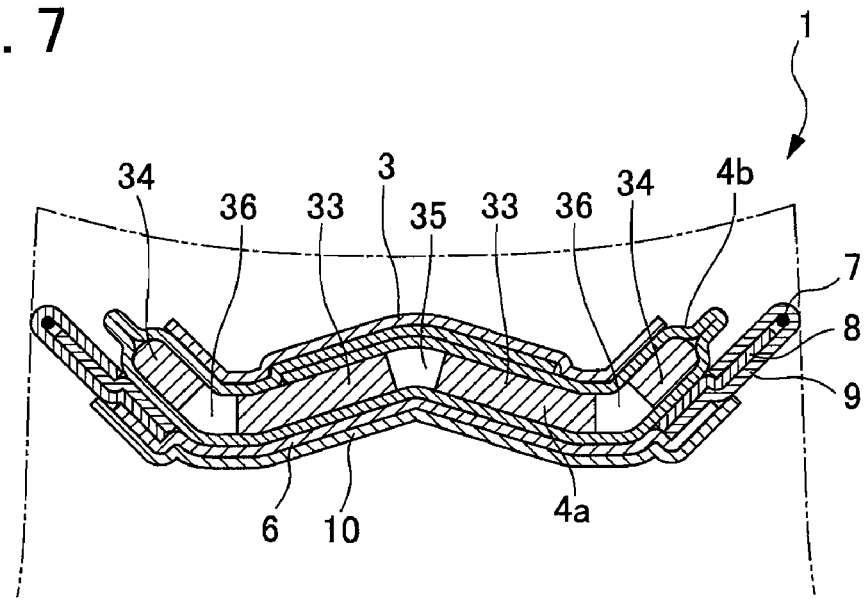
FIG. 7 illustrates that the disposable diaper which is deformed according to the present embodiment.
Figure 8:
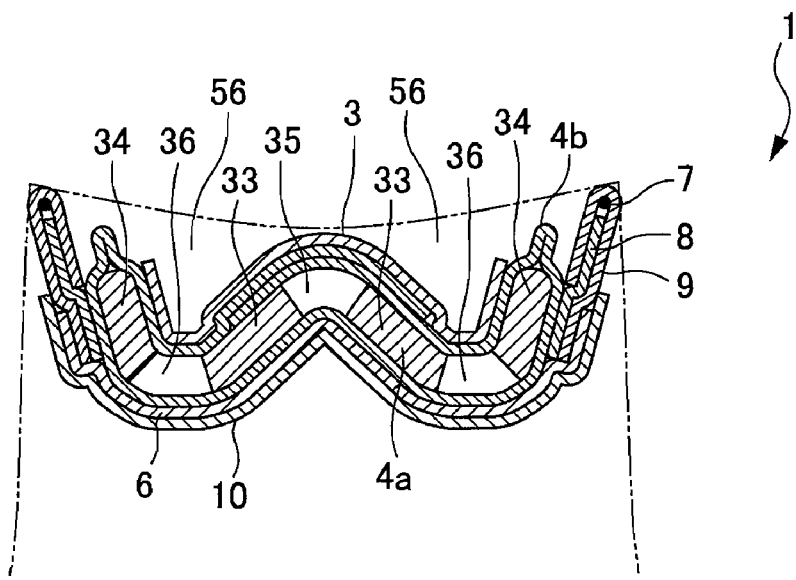
FIG. 8 illustrates that the disposable diaper which is deformed according to the present embodiment.
Figure 9:
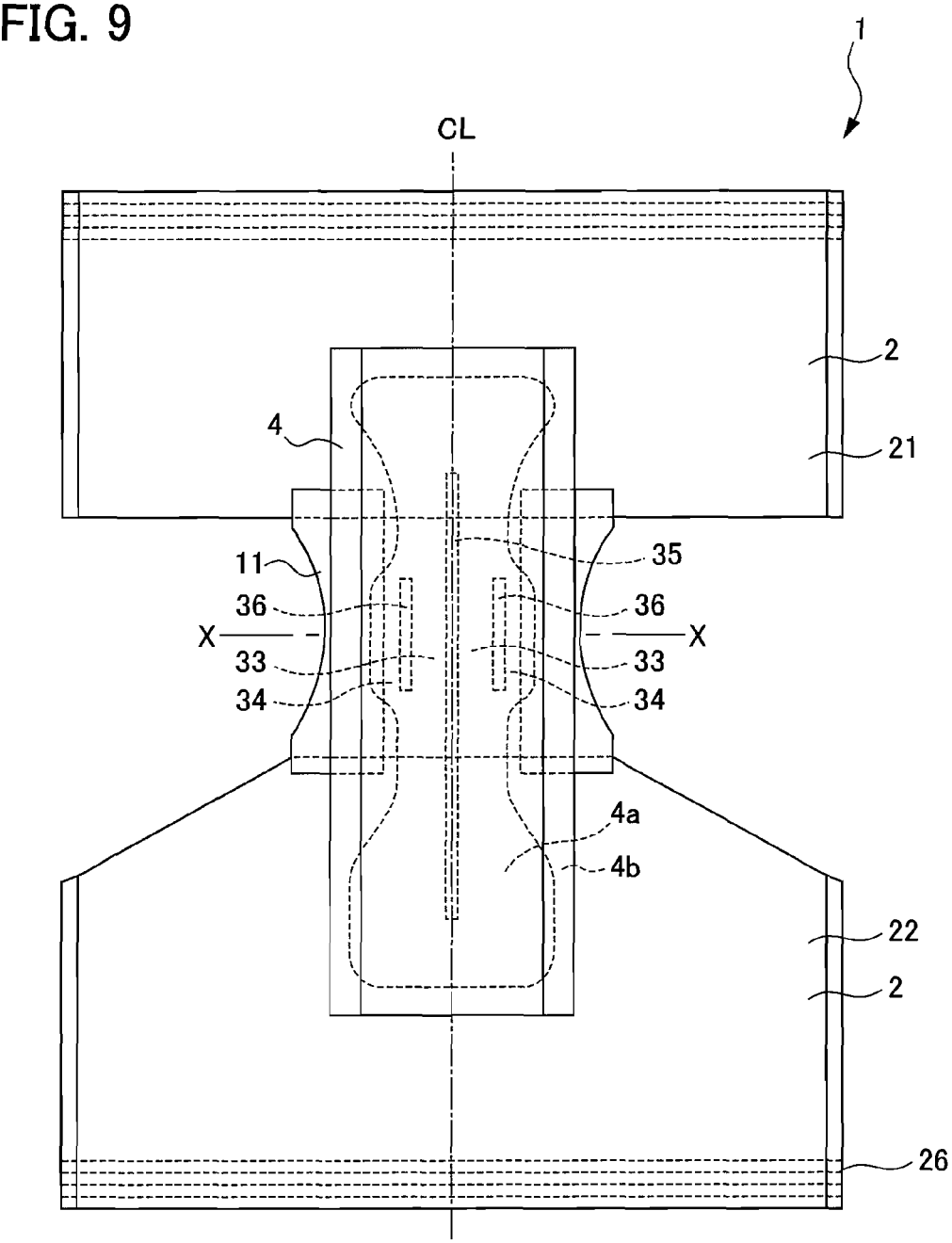
FIG. 9 is a development view illustrating a disposable diaper according to another embodiment in a developed status.
Figure 10:
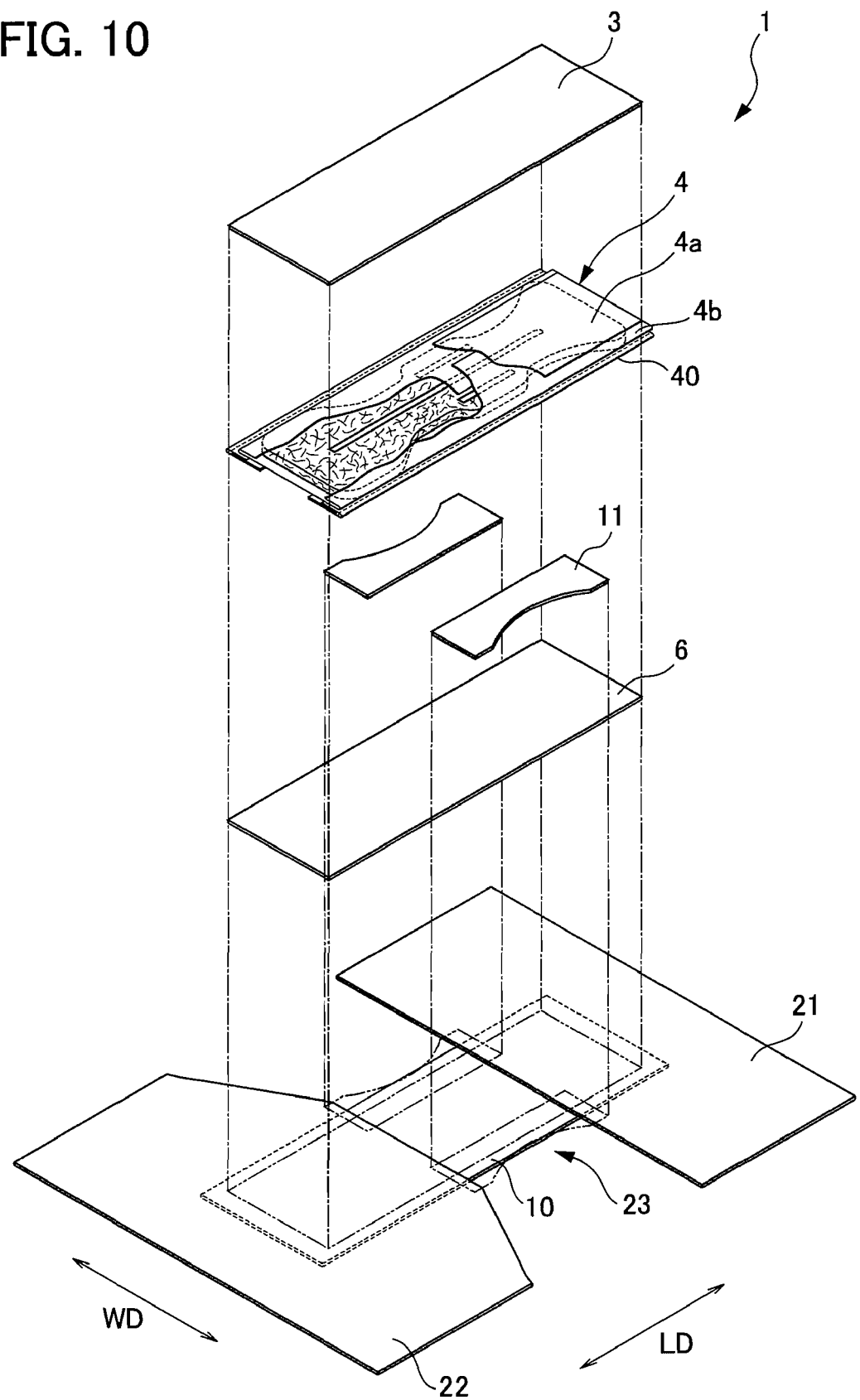
FIG. 10 is an exploded view illustrating the disposable diaper according to another embodiment.
Figure 11:
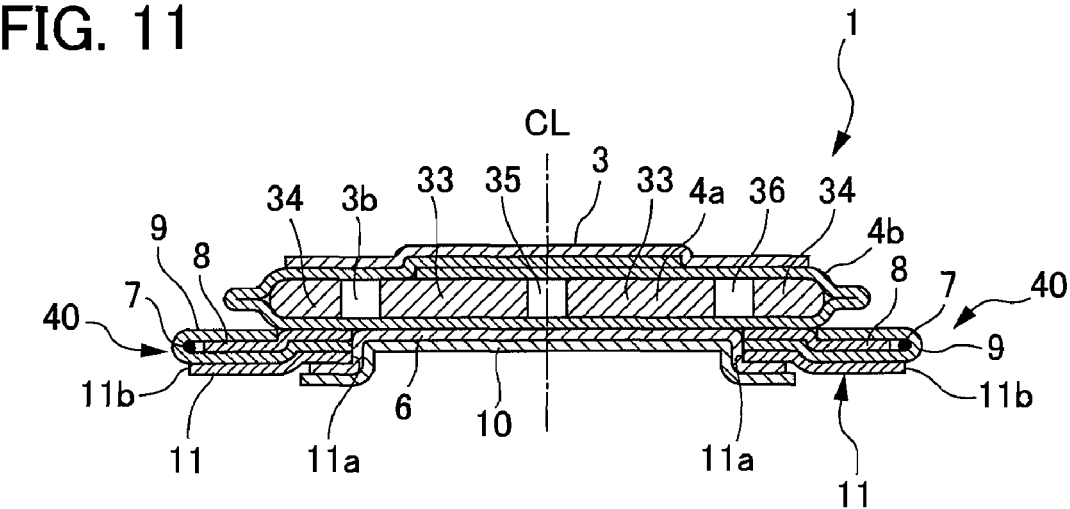
FIG. 11 is a cross-sectional view taken along X-X in FIG. 9.
Figure 12:
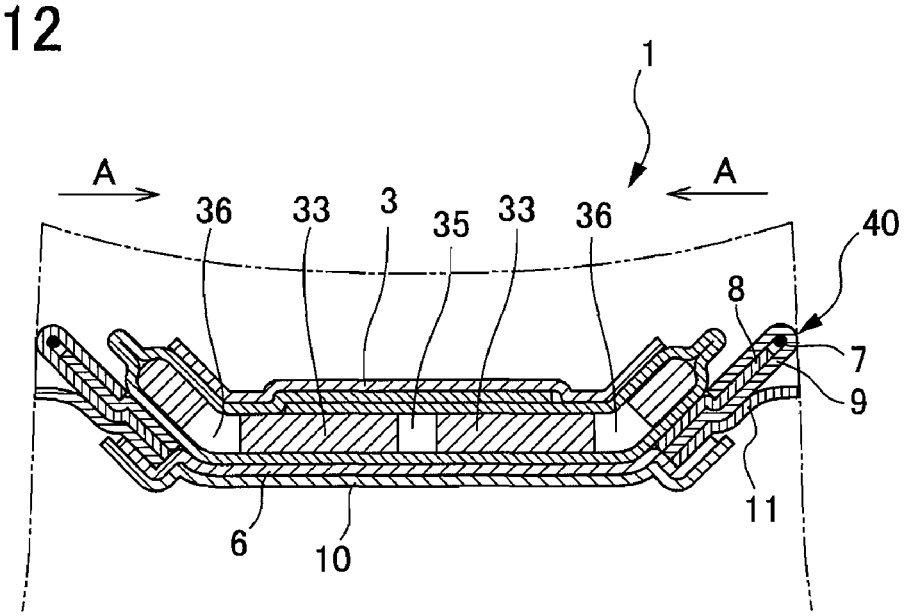
FIG. 12 illustrates that the disposable diaper which is deformed according to another embodiment.
Figure 13:
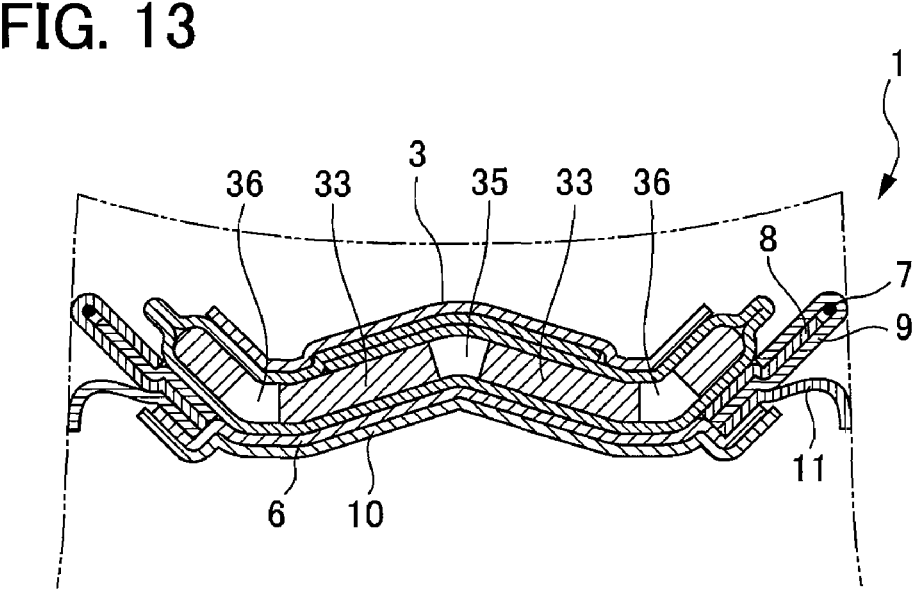
FIG. 13 illustrates that the disposable diaper which is deformed according to another embodiment.
Figure 14:
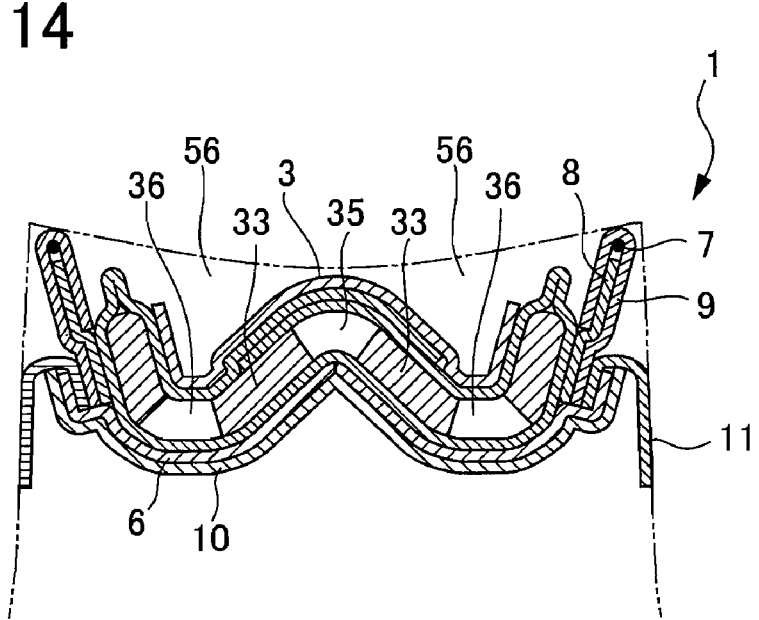
FIG. 14 illustrates that the disposable diaper which is deformed according to another embodiment.
Figure 15:
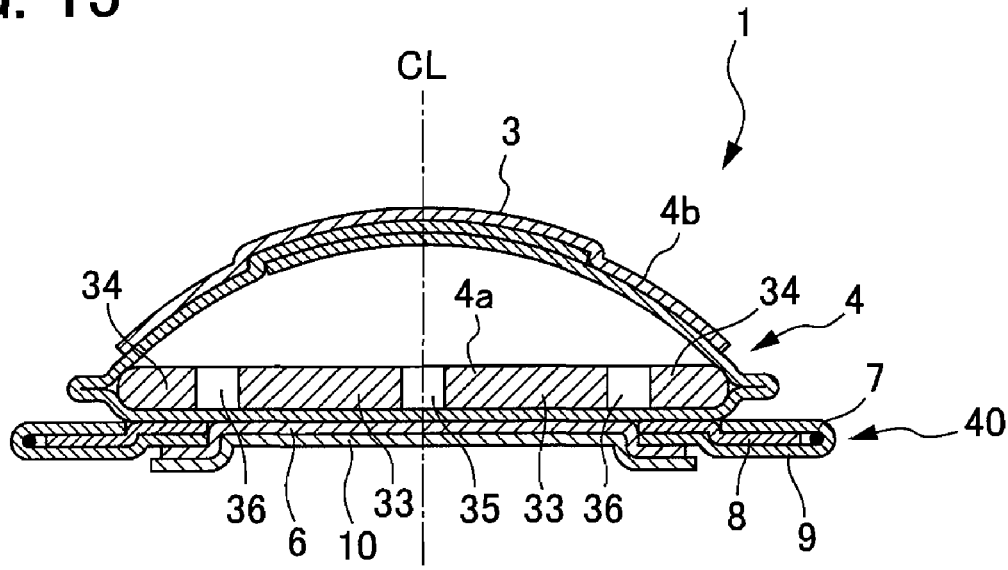
FIG. 15 illustrates a variation of the disposable diaper according to the present embodiment.
Figure 16:
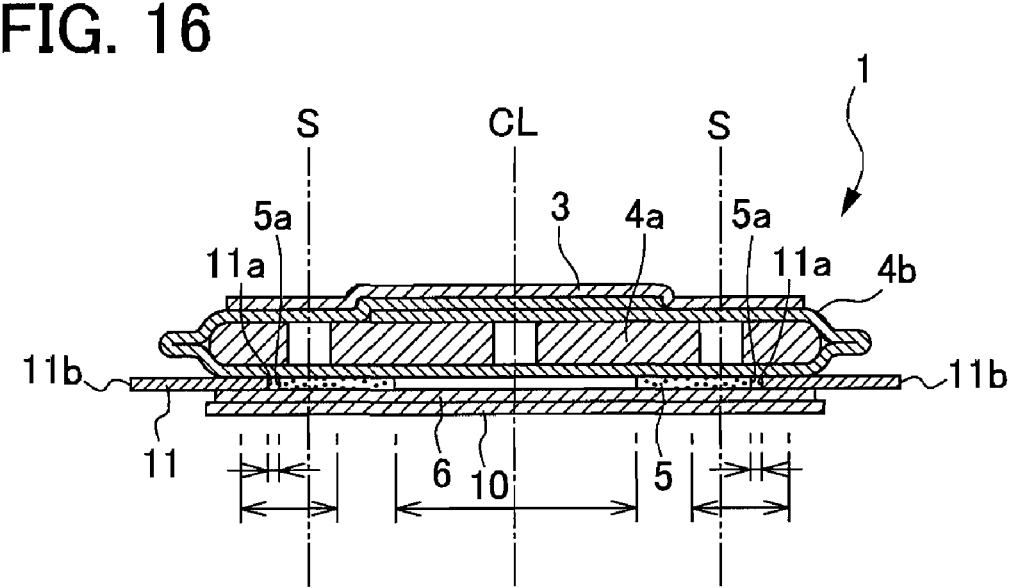
FIG. 16 is a schematic view illustrating a relation between absorbent body and a stretch sheet in the disposable diaper of another embodiment.
Figure 17:
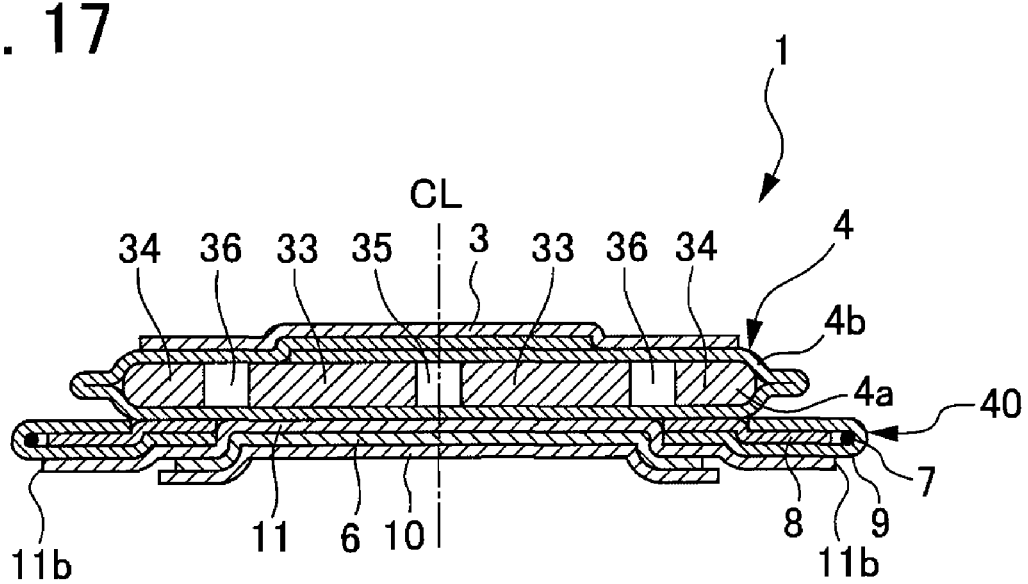
FIG. 17 illustrates a variation of the disposable diaper according to another embodiment.
Figure 18A:
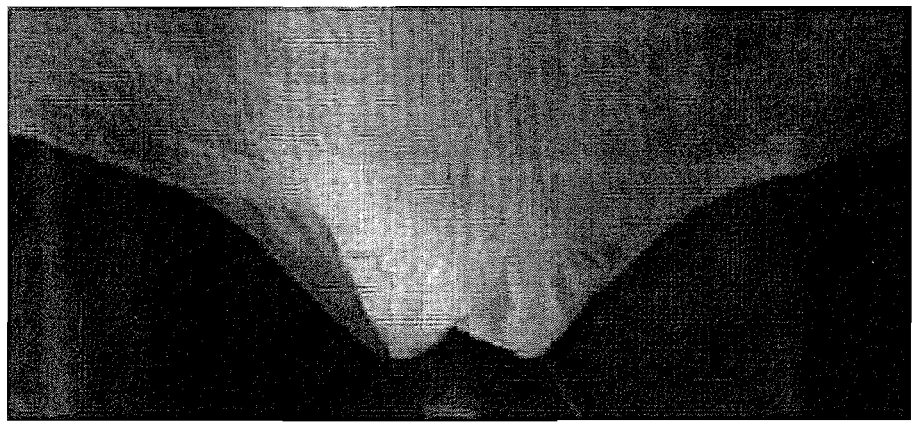
FIG. 18A illustrates an example of the present invention.
Figure 18B:
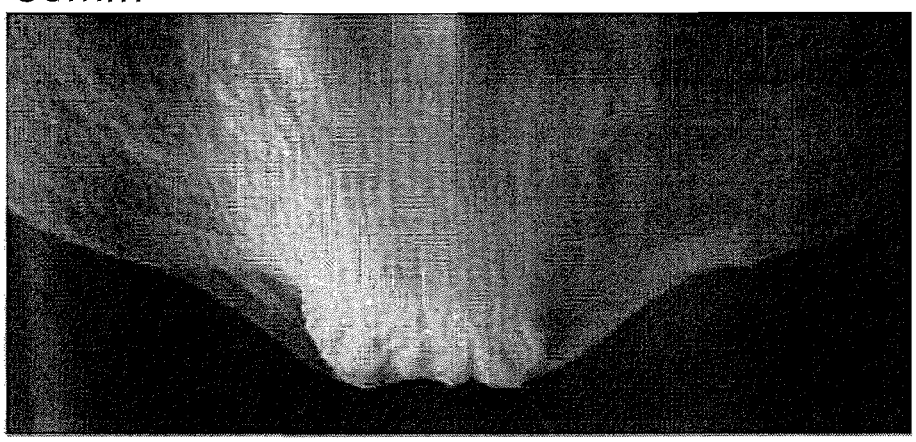
FIG. 18B illustrates an example of the present invention.
Figure 18C:
FIG. 18C illustrates an example of the present invention.

FIG. 1 is a perspective view illustrating a disposable diaper according to a first embodiment. FIG. 2 is a development view illustrating a developed disposable diaper according to the first embodiment. FIG. 3 is an exploded view illustrating the disposable diaper according to the first embodiment. FIG. 4A is a front view illustrating an absorbent body of the disposable diaper according to the first embodiment. FIG. 4B is a cross-sectional view taken along X-X in FIG. 4A. FIG. 5 is a cross-sectional view taken along X-X in FIG. 2. FIG. 6 illustrates that the disposable diaper according to the first embodiment is attached to a user and a force is applied to a crotch region and the crotch region is deformed. FIG. 7 illustrates a further deformed crotch region after the status shown in FIG. 6. FIG. 8 illustrates a further deformed crotch region after the status shown in FIG. 7 in which the absorbent body is bent to have a W-letter shape. FIG. 9 is a development view illustrating a disposable diaper according to a second embodiment in a developed status. FIG. 10 is an exploded view illustrating the disposable diaper according to the second embodiment. FIG. 11 is a cross-sectional view taken along X-X in FIG. 9. FIG. 12 illustrates that the disposable diaper according to the second embodiment is attached to a user and a force is applied to a crotch region and the crotch region is deformed. FIG. 13 illustrates a further deformed crotch region after the status shown in FIG. 12. FIG. 14 illustrates a further deformed crotch region after the status shown in FIG. 13 in which absorbent body is bent to have a W-letter shape. FIG. 15 is a first modified embodiment of the disposable diaper according to the first embodiment in which a skin-contacting face sheet is loosened. FIG. 16 is a schematic view illustrating a relation between absorbent body and a stretch sheet in the disposable diaper of the second embodiment. FIG. 17 illustrates a not-skin-contacting face of the absorbent body entirely covered by the stretch sheet of the disposable diaper according to the second embodiment. FIG. 18A illustrates a disposable diaper according to a first example having a W-letter shape of a favorable cross section. FIG. 18B illustrates a disposable diaper according to a second comparative example having no W-letter cross section. FIG. 18C illustrates a disposable diaper 1 having a W-letter cross section has an excessively-high height toward an excretory part.

1. First Embodiment

1.1. Entire Structure

The entire structure of a disposable diaper as an example of the absorbent article of the present invention is explained referring to FIGS. 1 to 4A. As shown in FIG. 1 and FIG. 2, the disposable diaper 1 includes: a chassis 2 that forms an outer shape thereof and that has a front torso surrounding region 21 and a rear torso surrounding region 22; a crotch region 23 positioned at a position corresponding to a crotch section of a user; and an absorbent body 4 that extends from the front torso surrounding region of the chassis 2 to the rear torso surrounding region along the longitudinal direction.

Also, as shown in FIG. 3, the disposable diaper 1 includes an elastic member 7 that is provided at a crotch region 23. The elastic member 7 forms a leakage preventing gather 40. Additionally, on a skin-contacting face of an absorbent body core 4a, a cover sheet 4b and a top sheet 3 are arranged sequentially constituting a skin-contacting face sheet according to the present invention. On a non-skin-contacting face of an absorbent body core 4a, a back sheet 6 is arranged constituting a non-skin-contacting face sheet according to the present invention.

As shown in FIG. 4A, the absorbent core 4a of the substantially rectangular absorbent body 4 arranged on the crotch 23 includes: a first narrow width section 31; a second narrow width section 32; a center low rigidity section 35 on a center line CL equally dividing the disposable diaper 1 in the width direction; and a pair of lateral low rigidity sections 36 which is formed on both sides in the width direction of the center low rigidity section at substantially regular intervals.

1.2. Chassis

As shown in FIG. 1 or FIG. 2, the chassis 2 includes joint sections 24 at which side edges of the front torso surrounding region 21 and the rear torso surrounding region 22 are partially joined to each other. In other words, the front torso surrounding region 21 is joined to the rear torso surrounding region 22 by intermittently joining the joint sections 24a and 24a' of the front torso surrounding region 21 to the joint sections 24b and 24b' of the rear torso surrounding region 22 by ultrasonic sealing for example. As a result, the chassis 2 is formed to have a pants-like shape. The chassis 2 partially includes threadlike elastic members 26 extending in the width direction to have a predetermined interval thereamong in the longitudinal direction. The crotch region 23 is composed of a stretching sheet.

1.3 Absorbent Body

1.3.1. Narrow Width Section

As shown in FIG. 3, the absorbent body 4 is substantially rectangular and composed of the absorbent core 4a and the liquid-permeable cover sheet 4b covering the absorbent core 4a. As shown in FIG. 4A, the absorbent core 4a has an oblong shape including a straight line having a predetermined length along which side edges 53a and 54a extend from the front edge 50 of absorbent core 4a in the longitudinal direction; the first concave section continuing from this straight line to protrude to the inner side in the width direction; a convex section continuing from this first concave section to protrude to the outer side in the width direction; the second concave section continuing from this convex section to protrude to the inner side in the width direction; and a straight line having a predetermined length continuing from this second concave section to extend in the longitudinal direction. This first concave part corresponds to the first narrow width section 31 and the second concave part corresponds to the second narrow width section 32.

The center absorbing section 39 has side regions 34 extending from the lateral low rigidity sections 36 to the outer sides of the absorbent body 4 in the width direction to reach the side edges 53b and 54b; and the center region 33 extending from the center low rigidity section 35 to the lateral low rigidity section 36. Specifically, the center absorbing section 39 includes the center regions 33 provided at the center part in the width direction to sandwich the center low rigidity section 35; and the side region 34 provided at the outer parts in the width direction and provided at the outer sides of the lateral low rigidity section 36.

The "narrow width section" includes the first narrow width section 31 and the second narrow width section 32. The term "narrow(er) width" means a part that has a narrower width than those of other parts of the absorbent body. The first narrow width section 31 and the second narrow width section 32 are formed by gradually reducing the width from the front torso surrounding region-side absorbing section 37 or the rear torso surrounding region-side absorbing section 38 of the absorbent body 4 toward the center absorbing section 39.

1.3.2. Center Absorbing Section

The absorbent body 4 includes the center absorbing section 39 at the center in the longitudinal direction. The center absorbing section 39 is a part of the absorbent body 4 arranged in the crotch 23.

The outer edges 53b and 54b of the center absorbing section 39 protrude to outer sides in the width direction and being wider than the first narrow width section 31 and the second narrow width section 32, and the outer edges thereof in the width direction are formed in straight lines. Thus the center absorbing section 39 has, at the front torso surrounding region side, the front torso surrounding region-side absorbing section 37 and has, at the rear torso surrounding region-side, the rear torso surrounding region-side absorbing section 38. The center absorbing section 39 has a length in the width direction for an adult of 55 to 225 mm. And the absorbent body 4 preferably has a length in the longitudinal direction of 50 mm to 300 mm. The reason is that the center absorbing section 39 having an excessively-large size causes an uncomfortable feeling or stiff feeling when the disposable diaper 1 is worn by a user while the center absorbing section 39 having an excessively-small size cannot satisfy a required absorption performance.

Outer edges 54b and 53b at the side regions 34 are preferably shaped to have a straight line along the longitudinal direction. However, the present invention is not limited to this. For example, the outer edges 54b and 53b also may be shaped to have a semicircular shape drawing a gentle curve. The center absorbing section 39 is a part that is deformed, when the disposable diaper 1 is worn by a user, to have a W-letter shape as described later.

1.3.3. Center Low Rigidity Section

The center low rigidity section 35 is shaped to have a straight line along the center line CL along which the absorbent body core 4a is halved in the width direction. The center low rigidity section 35 may be a region having a low rigidity at which the absorbent body 4 is bent. For example, the center low rigidity section 35 may be a region having a thin thickness, a low basis weight portion, a low density portion, a region including a great number of small holes, or a region in which absorbent body has no basis weight.

The center low rigidity section 35 preferably has a length in the longitudinal direction of 100 mm or more and more preferably of 200 mm to 450 mm for example. The center low rigidity section 35 has a length in the width direction of 5 mm to 15 mm for example. The center low rigidity section 35 preferably has a length in the width direction within a range of 50% or less of the length of the absorbent body 4 in the center absorbing section 39 in the width direction and has a length more preferably in a range from 7 mm to 12 mm.

As shown in FIG. 5, the absorbent body 4 is obtained by covering the absorbent core 4a by the cover sheet 4b. The back face of the absorbent body 4 is adhered with a back sheet. The center low rigidity section 35 is formed in a straight line along the center line CL at which the absorbent body 4 is halved in the width direction. An area in the vicinity of the center low rigidity section 35 is preferably not joined with the back sheet 6. The absorbent body 4 is structured so that an area in the vicinity of a side region 34 of the absorbent body 4 (which will be described later) is adhered to the back sheet 6 by a pair of adhesion sections 5. The respective adhesion sections 5 are preferably spaced with a distance of 10 mm to 60 mm.

1.3.4. Lateral Low Rigidity Section

The lateral low rigidity sections 36 are formed to extend in the center absorbing section 39 in the longitudinal direction. The lateral low rigidity sections 36 are formed at both sides of the center low rigidity section 35 in the width direction. Specifically, the center absorbing section 39 includes the two lateral low rigidity sections 36 that sandwich the center low rigidity section 35. The lateral low rigidity sections 36 are formed to have a shorter length in the longitudinal direction than that of the center low rigidity section 35. The lateral low rigidity sections 36 are a space as in the center low rigidity section 35. In other words, the lateral low rigidity sections 36 are slits. The lateral low rigidity sections 36 may be, as in the above-described center low rigidity section 35, a region having low rigidity at which the absorbent body 4 can be bent. For example, the lateral low rigidity sections 36 may be a region having a thin thickness, a low basis weight portion, a low density portion or a region including a great number of small holes.

The lateral low rigidity section preferably has a width in a range from 3 mm to 15 mm and more preferably in a range from 5 mm to 10 mm. The lateral low rigidity section preferably has a length in a range from 45 mm to 215 mm and more preferably in a range from 55 mm to 150 mm. A width narrower than 3 mm causes an insufficient bending margin required for the absorbent body to be bent to cause some cases in which the absorbent body cannot be bent in a regular manner. For example, in order to bend an absorbent body having a thickness of 3 mm by 180 degrees, a low rigidity section for the absorbent body must have a width of 6 mm, which is two times longer than 3 mm. A width of 15 mm or more may hinder the absorbability of the crotch section.

The total sum of an area of the center low rigidity section 35 and an area of the lateral low rigidity sections 36 is preferably 50% or less of the total sum of the area of the center absorbing section 39. When the total sum of an area of the center low rigidity section 35 and an area of the lateral low rigidity sections 36 is higher than 50% of the total sum of the area of the center absorbing section 39, the absorbability may decline to cause the leakage of excretory substance, which is not preferred.

The lateral low rigidity sections 36 functions to guide the deformation at the center absorbing section 39 in the thickness direction and also functions as a region at which the center region 33 and the side region 34 are bent during the deformation (which will be described later).

1.3.5. Side Region

The side regions 34 preferably have a length in the width direction in a range from 10 mm to 45 mm. The side regions 34 are a region that is deformed, in the wearing condition of the disposable diaper 1, so that ends of outer sides in the width direction of the respective side regions 34 are raised in the thickness direction. Specifically, the side regions 34 are deformed at the lateral low rigidity sections 36 that are formed at the inner sides in the width direction of the side regions 34.

1.3.6. Center Region

The center region 33 preferably has a length in the width direction in a range from 10 mm to 45 mm. A ratio between the length of the side region 34 (which will be described later) and the length in the width direction of the center region 33 is preferably within a range as described below.
Side region 34: center region 33=35 to 65:65 to 35

The center regions 33 is a region at which, in the wearing condition of the disposable diaper 1, ends at the inner sides in the width direction of the respective center regions 33 are deformed so that the ends are raised in the thickness direction. Specifically, the center regions 33 is deformed so that the center regions 33 are bent at the center low rigidity section 35 formed at one side in the width direction of the center regions 33 and at the lateral low rigidity section 36 formed at the other side in the width direction of the center regions 33. The term "thickness direction" means a direction along the thickness of an absorbent body prior to the deformation as described above.

1.3.8. Leakage Preventing Gather

As shown in FIG. 3, the leakage preventing gather 40 including the elastic member 7 is arranged along the side edge in the width direction of the crotch region 23. As shown in FIG. 5, the leakage preventing gather 40 is provided at the side edge of the outer side in the width direction of the absorbent body 4 along the longitudinal direction of the absorbent body 4.

The leakage preventing gather 40 is prepared in the manner as described below. First, the side sheet 9 is provided between the absorbent body 4 and the back sheet 6. The side sheet 9 sandwiches the side film 8 and at least one elastic member 7 in a tensile status to cover the side film 8 and the elastic members 7. Next, as shown in FIG. 5, the side sheet 9 is folded into two parts so that the crease-side is provided at the outer side, and the inner side includes one end and the other end of the side sheet 9. Then, the one end abutted to the back sheet 6 and the other end abutted to the absorbent body 4 are fixed at the adhesion section 5 by hot melt adhesive agent or the like so that the side sheet 9 is sandwiched by the absorbent body 4 and the back sheet 6. As a result, the leakage preventing gather 40 is prepared.

Then, the elastic member 7 in the leakage preventing gather 40 is stretchable to raise the leakage preventing gather 40 toward the skin-contacting face. The raised leakage preventing gather 40 functions, in the crotch of a user, to fill a gap between the absorbent body 4 and the crotch to prevent excretory substance from leaking from the gap.

The side edge of the leakage preventing gather 40 including the elastic member 7 is deformed, in order to maintain the condition in which the diaper is abutted to groins of a user's body, so that the side edges of the crotch region 23 are raised to the user's body while being pulled by the leakage preventing gather 40. Specifically, the absorbent body 4 provided at the crotch region 23 is also similarly deformed so that the side edges at the absorbent body 4 are raised to the user's body. Since the leakage preventing gather 40 is provided along the side edge in the width direction of the absorbent body 4, the absorbent body 4 is deformed in the manner as described above. Specifically, the leakage preventing gather 40 supports the deformation of the absorbent body 4 so that the side edges of the absorbent body 4 are raised to the user's body.

1.3.8. Skin Contacting Face-Side Sheet

In the crotch region 23, the skin-contacting face of the absorbent core 4a has the cover sheet 4b for covering the absorbent core 4a. The cover sheet 4b consists of a liquid-permeable nonwoven cloth and is provided so as to entirely cover the absorbent core 4a. Specifically, the cover sheet 4b is a sheet that is provided at the skin-contacting face of the absorbent core 4a and is not fully adhered to the top face of the absorbent core and thus is provided while being partially loosened and partially adhered.

The skin-contacting face of the cover sheet 4b has the top sheet 3. The top sheet 3 is adhered to the cover sheet 4b. As in the cover sheet 4b, the top sheet 3 consists of a liquid-permeable nonwoven cloth and can be easily stretched. The top sheet 3 is also adhered to the skin-contacting face of the cover sheet 4b and thus is provided while being partially loosened and partially adhered as in the cover sheet 4b.

When the top sheet 3 is fixed by a chuck with an interval of 50 mm and is pulled with a tensile speed of 100 mm/minute, the top sheet 3 shows a tensile strength of 0.58 N/50 mm when being stretched by 10%. When the not-skin-contacting face sheet 10 (which will be described later) is pulled under the same conditions as those for the top sheet 3, the not-skin-contacting face sheet 10 shows a tensile strength of 7.13 N/50 mm. Thus, when compared with the not-skin-contacting face sheet 10, the top sheet 3 can be easily stretched in the width direction of the manufacturing direction of the top sheet 3.

The tensile strength of the top sheet is measured by the following procedures. To measure the initial strength in the width direction of a product made therefrom, a test piece is obtained from the sheet of 100 mm in the width direction and 50 mm in the lengthwise direction. The test piece is fixed by a chuck with an interval of 50 mm and is pulled with a tensile speed of 100 mm/minute. The tensile strength in a case of an expansion to 110% is read off and compared. An autograph-type tensile test machine (AG-1 kNI manufactured by Shimadzu Corporation) is used for the tensile test.

As described above, the sheet provided at the skin-contacting face can be easily stretched and is provided while being loosened. Thus, the deformation of the absorbent body 4 in the thickness direction is prevented from being hindered. Specifically, the deformation of the center regions 33 in the center absorbing section 39 in which the center regions 33 protrude from the center low rigidity section 35 in the thickness direction (to the skin-contacting face) is prevented from being hindered. As shown in FIG. 15, when the diaper is not worn by a user, the cover sheet 4b or the like may be significantly loosened. Specifically, the length of the cover sheet 4b in the width direction is longer than that of the absorbent body 4 in the width direction and the length in the width direction of the top sheet 3 as a skin-contacting face sheet is longer than that of the absorbent body 4 in the width direction. The cover sheet can thus be loosened at the skin-contacting face of the absorbent body 4, and the absorbent body 4 is easier to bend into W-letter shape when an inward force is given in the width direction.

1.3.9. Not-Skin Contacting Face-Side Sheet

In the crotch region 23, the not-skin-contacting face of the absorbent body 4 has the liquid-impermeable back sheet 6.

The back sheet 6 consists of a breathable film sheet having a low stretching property and is adhered to the not-skin-contacting face of the absorbent body 4 while being stretched.

The not-skin-contacting face of the back sheet 6 has the outer covering sheet 10 that has a high initial tensile strength. The outer covering sheet 10 is adhered to the back sheet 6 while being stretched. Specifically, the outer covering sheet 10 is provided at the not-skin-contacting face at a part or the entirety in the center absorbing section 39 of a range from the center region 33 to the side region 34.

1.3.10. Modified Embodiment of Absorbent Body

Hereinafter, with reference to FIG. 6 to FIG. 8, the deformation of the absorbent body 4 in the wearing condition will be described. As shown in FIG. 6, the disposable diaper 1 at the wearing stage is pulled to the upper side in FIG. 6 and receives a force to the inner side in the width direction from legs of a user. In other words, the crotch region 23 at the wearing stage is deformed to have a shorter length in the width direction. As a result, both side edges at the absorbent body 4 are firstly deformed so that the side edges are raised to the user's body in the thickness direction.

Specifically, the respective side regions 34 in the center absorbing section 39 are deformed so that ends at the outer sides in the width direction of the side regions 34 are raised at the respective lateral low rigidity sections 36 formed at the inner side in the width direction toward the user's body in the thickness direction. As a result, the absorbent body 4 is deformed to have a U-like cross section in the thickness direction, as shown in FIG. 6.

Next, when the disposable diaper 1 is further pulled to the upper side, the absorbent body 4 receives a further force from the user's legs to the inner side in the width direction. In other words, the crotch region 23 is deformed to have a further shorter length in the width direction. As a result, the center section in the absorbent body 4 is deformed so as to protrude to the user's body in the thickness direction.

Specifically, in order to allow the center low rigidity section 35 in the center absorbing section 39 to protrude to the user's body in the thickness direction, the respective center regions 33 are deformed so that the respective center regions 33 are bent at the respective lateral low rigidity sections 36 formed at the outer sides in the width direction and the center low rigidity section 35 formed at the inner side in the width direction inner side. Specifically, the respective side edges at the center low rigidity section 35, which are at the center region 33 at one side and the other side in the width direction of the center low rigidity section 35, are deformed so as to be raised to the user's body in the thickness direction. The reason why the respective side edges in the center regions 33 at the center low rigidity section 35 are deformed so as to be raised to the user's body in the thickness direction is that the not-skin-contacting face of the absorbent body 4 has a not-skin contacting face-side sheet such as the back sheet 6 having higher initial tensile strength than that of the top sheet 3 and the cover sheet 4b which are sheets provided at the skin-contacting face in the absorbent body 4, and the outer covering sheet 10 while the not-skin contacting face-side sheets being stretched. As a result, as shown in FIG. 7, the absorbent body 4 is deformed to have a W-letter shaped cross section in the thickness direction.

When a user wearing the disposable diaper 1 has a standing posture, the crotch region 23 is deformed to have a very short length in the width direction. As s result, the side edges of the absorbent body 4 are deformed so as to be further raised to the user's body in the thickness direction and the center section of the absorbent body 4 are deformed to be further raised to the user's body in the thickness direction.

Specifically, the respective side regions 34 in the center absorbing section 39 are deformed so that the side regions 34 are bent at the respective lateral low rigidity sections 36 formed at the inner sides in the width direction to allow the ends of the respective side regions 34 at the outer sides in the width direction to be further raised to the user's body in the thickness direction. Furthermore, in order to protrude the center low rigidity section 35 in the center absorbing section 39 to the user's body in the thickness direction, the respective center regions 33 are deformed so that the center regions 33 are bent at the respective lateral low rigidity sections 36 formed at the outer sides in the width direction and the center low rigidity section 35 formed at the inner side in the width direction. Specifically, the respective side edges at the center low rigidity section 35 at the center region 33 at one side and the other side in the width direction of the center low rigidity section 35 are deformed so as to be raised to the user's body in the thickness direction. As a result, as shown in FIG. 8, the absorbent body 4 is deformed to have a more W-letter shaped cross section in the thickness direction.

When the diaper is worn by the user continuously, the leakage preventing gather 40 is maintained so that the side edges of the leakage preventing gather 40 including elastic member 7 are abutted with the groin region of the user's body. Thus, as shown in FIG. 8, side edges in the center absorbing section 39 in the absorbent body 4 raised to the user's body in the thickness direction are maintained. When the user's legs are opened or closed in the wearing condition, a force is applied in the direction of arrow A of FIG. 6 to cause the absorbent body 4 to be deformed to have a W-letter shape. Thus, when the user stands up or walks for example, the center section of the absorbent body 4 in the width direction protrudes to the user's body in the thickness direction and is abutted with an excretory part or the like.

As described above, the center absorbing section 39 in the absorbent body 4 is deformed to have a W-letter shape. The center section of the center absorbing section 39 in the width direction is deformed to protrude in the thickness direction and is abutted with an excretory part of the user's body. Side edges of the center absorbing section 39 at outer sides in the width direction are deformed to be raised in the thickness direction so that the edges can be abutted with the user's body. By the deformation of the absorbent body 4, the absorbent body 4 can preferably absorb the excretory substance discharged from the excretory part, for example, and can suppress the leakage of the excretory substance from the user's body in the width direction.

According to the disposable diaper 1 of this embodiment, the absorbent body 4 is deformed to have a W-letter shaped cross section in the thickness direction. Thus, a part in the vicinity of the center low rigidity section 35 as a convex section in the W-letter shape is close to or abutted to the excretory part of the user's body. Thus, the disposable diaper 1 can immediately absorb the excretory substance from the excretory part can suppress excretory substance from streaming down on the skin of the user. Furthermore, the concave section in the W-letter shape formed by the center low rigidity section 35 and the lateral low rigidity section 36 stores excretory substance and also can disperse the excretory substance in the front-and-rear direction. Furthermore, the absorbent body 4 is deformed to have a W-letter shape and thus the absorbent body 4 positioned close to the excretory part can have a sufficient absorption area.

According to the disposable diaper 1 of this embodiment, the absorbent body 4 is deformed to have a W-letter shaped cross section in the thickness direction. Thus, the crotch region 23 has a preferably short length in the width direction. Thus, feeling of pressure at the crotch section can be reduced. Furthermore, in accordance with a movement of a user (e.g., opening or closing of legs), the absorbent body 4 stretches in the width direction while changing the depth of the W-letter shape, thus providing an increased uncomfortable feeling.

2. Second Embodiment

The absorbent article of the second embodiment is an absorbent article that is different from that of the first embodiment in that the diaper of the first embodiment includes a stretch sheet. Hereinafter, the same components and parts as those of the first embodiment are designated by the same numerals and the corresponding descriptions similarly apply.

2.1. Stretch Sheet

As shown in FIG. 9 and FIG. 11, the disposable diaper 1 includes a stretch sheet 11 extending from both side edges of the center absorbing section 39 of the absorbent body 4 to the outer sides in the width direction. The stretch sheet 11 is not joined to the absorbent body 4. The stretch sheet is at least stretchable and elastic in the longitudinal direction of the disposable diaper 1. The stretch sheet 11 has a length adjusted to be shorter than the length of the back sheet 6 superposed on the stretch sheet 11.

As shown in FIG. 16, the stretch sheet 11 is adhered to the back sheet 6 and extends from a position 50 mm away in the width direction from the center S in the width direction of the lateral low rigidity section 36 to a point 27.5 mm to the inner side in the width direction. More preferably, the stretch sheet 11 is arranged within 20 mm outward in the width direction and 10 mm inward in the width direction of the center S. In this case, a distance between the side edges 11a of the stretch sheet is 70 mm to 110 mm.

It is noted that the absorbent body 4 and the stretch sheet 11 have therebetween the leakage preventing gather 40 (which will be described later) and thus the absorbent body 4 is not directly joined to the stretch sheet 11. In FIG. 16, in order to simply illustrate the joint position, the leakage preventing gather 40 is not shown. In an actual case, the stretch sheet 11 is adhered to be sandwiched between the side sheet 9 constituting the leakage preventing gather 40 and the back sheet 6. The center of the lateral low rigidity section 36 in the width direction means, for example, a position 3.75 mm away from one end of the lateral low rigidity section 36, when the lateral low rigidity section 36 has a width of 7.5 mm.

As shown in FIG. 16, when the adhesion section 5 adhered with the absorbent body 4 and the back sheet 6 is assumed as a reference, the edge 5a of the adhesion section 5 at the outer side in the width direction and the side edge 11a of the stretch sheet 11 at the inner side in the width direction are adhered at a part at the outer side of the edge 5a of the adhesion section in a range of 15 mm to 0 mm in the width direction or at a part at the inner side of the edge 5a of the adhesion section in a range of 0 mm to 5 mm in the width direction. More preferably, the side edge 11a is preferably away from the edge 5a of the adhesion section by a distance of 10 mm to 5 mm. Specifically, the stretch sheet 11 and the adhesion section 5 may be separated from each other or may be superposed. The side end 5a of the adhesion section 5 is at the outer side in the width direction from the lateral low rigidity section 36 at which the diaper is bent.

The stretch sheet 11 has a plate-like shape having a predetermined length and is at least stretchable and elastic in the longitudinal direction of the diaper. In the crotch region 23, the stretch sheet 11 is provided at the outer side of the absorbent body 4 in the width direction and is not joined with the absorbent body 4. However, as shown in FIGS. 4A and 9, the absorbent body 4 has the longest width at the front torso surrounding region-side absorbing section 37 and the rear torso surrounding region-side absorbing section 38 and has the shortest width at the first and second narrow width sections. Thus, the stretch sheet can be placed at both sides in the width direction of the center absorbing section 39 of the absorbent body 4 having a narrower width. In this case, the center absorbing section 39 has the convex side regions 34 protruding in the width direction. However, the side region 34 and the stretch sheet 11 may be superposed. It is noted that the stretch sheet 11 must not be adhered to the side region 34.

As shown in FIG. 16, width direction outer edges 11b of the pair of stretch sheets 11 are placed so as to go over both outer edges of the absorbent body 4 in the width direction and to extend to outer sides in the width direction. The stretch sheet 11 is adhered to the back sheet 6 at both sides in the width direction of the back sheet 6 joined to the absorbent body 4.

The stretch sheet 11 extends to the outer side in the width direction of the side edge of the absorbent body 4. In other words, the stretch sheet 11 is placed at a face of the absorbent body 4 not abutted with a user's skin so that the stretch sheet 11 protrudes from the absorbent body. The width direction inner edge 11a of the stretch sheet is superposed on the side edge of the absorbent body 4. However, the width direction outer edge 11b is not superposed on the absorbent body. The stretch sheet 11 is provided so as to further extend in the absorbent body 4 longitudinal direction from both ends in the longitudinal direction of the center absorbing section 39.

As shown in FIG. 16 and FIGS. 18A to 18C, an interval between one width direction inner edge 11a and the other width direction inner edge 11a of the pair of stretch sheets 11 is preferably about 70 mm to 110 mm. When the interval is smaller than this range, the cross section is suppressed from having a W-letter shape. When the interval is larger than this range, the stretch sheets for maintaining the W-letter shape are excessively away from each other and thus the deformation of the center region cannot be controlled. Thus, the convex section formed from the center low rigidity section to extend to the user's body may have an excessively-high height to the user's body.

By the arrangement as described above, the diaper can follow the movement of the user's legs and can easily stretch. Thus, the absorbent body can be directly prevented from twisting or from being distorted due to the movement of user's legs.

The stretch sheet 11 is adjusted to have a shorter length than that of the back sheet 6. Specifically, the stretch sheet 11 has preferably a length 20% or more shorter than the length of the back sheet. If the stretch sheet 11 does not have such a shorter length at all or has a short length like that of the back sheet, the resultant absorbent body is planar or is abutted with the crotch section in an inverted V-like shape to increase a width at which the absorbent body has a contact with a user's skin or to cause the absorbent body to be abutted to the inner thigh, thus causing the user to experience an uncomfortable feeling.

Although the tensile strength of the stretch sheet 11 is different depending on the basis weight or rigidity of the or an existence or non-existence of a slit, when assuming that the crotch region has a length Y (i.e., the length of the back sheet in the crotch region), the stretch sheet 11 has a tensile strength of 0.5 N or more and 10 N or less and preferably a tensile strength in a range of 2 N to 7 N when the stretch sheet 11 is elongated to have a length of Y×95%. An excessively weak stress of the stretch sheet 11 prevents the side region 34 of the absorbent body 4 from being supported from the lower side to fail to provide a W-letter shape. An excessively strong stress of the stretch sheet 11 on the other hand causes a V-like shape or prevents the stretch sheet 11 from being sufficiently elongated to cause a gap between a user's skin and the absorbent body, causing a risk where excretory substance streams down the skin to leak.

The stretch sheet 11 preferably has the narrowest width of 10 mm or more and the widest width of about 100 mm and the outer edge is cut to correspond to the shape of a leg opening of a crotch section. This shape can allow a part corresponding to a complicated shape of a human body (e.g., crotch section, a part close to a groin) to have be abutted with the body in a plane.

In this embodiment, the stretch sheet 11 is obtained by joining the back sheet 6 as an unstretching nonwoven cloth provided at the back face of the absorbent body with a stretchable and elastic nonwoven cloth in the longitudinal direction of a resultant product while the components being stretched. However, the stretch sheet 11 is not limited to this so long as the stretch sheet 11 has a plane-like shape of 10 mm or more and can be stretchable and elastic in the longitudinal direction of the diaper. For example, the stretch sheet 11 also may be a single stretching nonwoven cloth, a complex sheet of two layers or more including a stretchable and elastic film or net, a plane-like member obtained by arranging a plurality of threadlike elastic members with a small pitch of 10 mm or less, or urethane foam. Alternatively, the entire crotch region also may be provided by a stretching member and a part other than a stretchable and elastic crotch part also may be processed so that this part is not stretchable or elastic.

2.2. Modified Embodiment of Stretch Sheet

Hereinafter, with reference to FIG. 12 to FIG. 14, the deformation of the absorbent body 4 in the wearing condition will be described. As shown in FIG. 12, when the stretch sheet 11 is worn by a user, the stretch sheet 11 extends along the crotch to the inner thigh of the user, while stretching in the longitudinal direction of the diaper. As shown in FIG. 13, when the disposable diaper 1 is pulled up to the crotch region, the stretch sheet 11 is abutted surface-to-surface to the inner thigh of the user. As shown in FIG. 14, when the disposable diaper 1 is completely pulled up to the user's body and is placed at the crotch of the user's body without causing an uncomfortable feeling at the crotch region 23, the width direction outer edge 11b of the stretch sheet is attached so as to face the not-skin-contacting face in the thickness direction of the absorbent body.

The absorbent article according to the second embodiment also includes the leakage preventing gather 40 as in the first embodiment. Thus, when the elastic member 7 of the leakage preventing gather 40 is stretched, the side region 34 of the absorbent body 4 is raised. The stretch sheet 11 is pulled up so as to support the raised side region 34 by the not-skin-contacting face. Thus, the side region 34 is stable to allow the absorbent body 4 to be stably bent in the thickness direction.

By the structure as described above, when the disposable diaper 1 is worn by a user, the side region 34 of the absorbent body 4 is raised to support the absorbent body 4 to be bent to have a U-like shape. Furthermore, an upper end of the edge of the outer side in the width direction of stretch sheet 11 to the user's body is always retained so as to have a contact with a groin of the user. When the diaper is worn by a user, the stretch sheet 11 is abutted surface-to-surface with the inner thigh of the user to function to block the lateral leakage of excretory substance. Furthermore, the stretch sheet 11 is placed in the vicinity of the side region 34 of the absorbent body 4 and at a position at which the W-letter shape is bent. Thus, even when the absorbent body 4 deformed to have the W-letter cross section extends in the lateral direction due to opening and closing of legs, the stretch sheet 11 is stretched to function to retain the deformed W-letter shape.

According to the disposable diaper 1 of this embodiment, the stretch sheet 11 is composed of a plane sheet of a width of 10 mm or more. Thus, the stretch sheet 11 can be abutted with a complicated shape of the crotch region of the user, not in lines but surface-to-surface extensively, thus preventing an occurance of a gap. In the wearing condition, the stretch sheet 11 is abutted with the inner thigh so as to fill the gap caused between the inner thigh and the disposable diaper 1. Since the absorbent body 4 and the back sheet 6 have therebetween the leakage preventing gather 40, even when excretory substance leaks from the leakage preventing gather 40, the stretch sheet 11 abutted with the inner thigh in a plane can block the excretory substance. Furthermore, since the sheet having a width of 10 mm is joined to the outer edge of the back sheet 6, a user's leg can be prevented from touching the gather or frill to provide a simpler appearance and to allow the diaper to be worn more comfortably, thus providing increased feeling of security.

First Modified Embodiment

As shown in FIG. 17, the stretch sheet 11 also functions as the back sheet 6, is adhered to the back face of the absorbent body 4, and can allow the width direction outer edge 11b of the stretch sheet to extend to the outer side in the width direction of the absorbent body 4 as in the above-described stretch sheet 11. A stretch sheet of the first modified embodiment may be adhered to the absorbent body 4 at the same position as that in the first embodiment. Specifically, a part in the vicinity of the center region 33 of the absorbent body 4 is not joined to the absorbent body 4 and only a part in the vicinity of the side region 34 can be adhered to the absorbent body 4. As in the first embodiment, the not-skin-contacting face sheet 10 is an unstretching sheet. Thus, the center region 33 of the absorbent body 4 can protrude in the user's body direction. By the structure as described above, labor required for providing the back sheet 6 can be eliminated to reduce the manufacture steps. Furthermore, the manufacture cost of the back sheet 6 also can be reduced.

3. Third Embodiment

An absorbent article of a third embodiment is different from that of the first embodiment in that a region having a thin thickness is formed as a low rigidity section. The region having a thin thickness is formed by reducing the thickness of the absorbent body. Specifically, the region having a thin thickness is formed by reducing the basis weight to cause the low rigidity section to have a lower fiber density than those of other parts of the absorbent body 4. The center low rigidity section 35 and the lateral low rigidity section 36 may mainly composed of, for example, pulp of natural fiber, or chemical fiber with a fiber length of 1 mm to 10 mm for which a ratio of the pulp and pulp mass/(pulp and SAP mass) to the absorbent body mass is 45% to 100%. The pulp basis weight may be in a range of 5 g/m$^2$ to 200 g/m$^2$ and is preferably 200 g/m$^2$. The region having a thin thickness may have a thickness of 0.1 mm to 2.0 mm. On the other hand, with regards to the fiber density of a part other than the region having a thin thickness as the center low rigidity section 35 and the lateral low rigidity section 36, in the case of pulp having a fiber length of 1 mm to 10 mm, a ratio of the pulp mass/(pulp and SAP mass) to the absorbent body mass may be 45% to 65%. In this case, the pulp basis weight may be within a range of 50 g/m² to 400 g/m² and the thickness may be within a range of 1.0 mm to 5.0 mm.

As described above, by reducing the basis weight so that the low rigidity section can have a lower fiber density than those of other regions of the absorbent body 4, the low rigidity section can have a thinner thickness than those of other regionsparts of the absorbent body 4. Thus, the absorbent body 4 has lower rigidity. As a result, when the diaper is worn by a user and the diaper receives a force from the inner thigh of the user to the inner side of the user's body, the absorbent body 4 is bent at the low rigidity section.

The third embodiment is the same as the first embodiment except for that the absorbent body 4 of the low rigidity section of the third embodiment is formed by the low rigidity section to have a thinner thickness than those of other regions of the absorbent body 4.

EXAMPLE

The following section will describe examples of the present invention. However, the examples are mere examples for favorable carrying out the present invention and do not limit the present invention in any way.

First Example

As shown in Table 1, widths of the side region 34 and the center region 33 of the absorbent body 4 were changed to evaluate the wearing feeling and whether the absorbent body has a clear W-letter shaped cross section or not. An absorbent body in this evaluation was prepared in the manner as described below. First, high absorbance polymer (e.g., polyacrylate-base or starch/acrylate-base one) including 80% or more absorbance polymer having a water absorption factor of 20 g/g or more and a grain size of 100 to 800 μm and hydrophilic fiber (e.g., ground pulp fiber or rayon fiber) were prepared. Then, the high absorbance polymer and the hydrophilic fiber were covered by the cover sheet 4b the cover sheet 4b as a hydrophilic sheet obtained by subjecting hydrophobic fiber (e.g., polyolefin-based one, polyester-base one) to a hydrophilic processing. In a first example, the lateral low rigidity section has a width of 7.5 mm and the center low rigidity section has a width of 10 mm. The side region 34 and the center region 33 both have a width of 23.8 mm. The absorbent body 4 of the first example has a total width of 120.2 mm.

TABLE 1

|  | First Example | Second Example | Third Example | Fourth Example | First Comparative Example | Fifth Example |
|---|---|---|---|---|---|---|
| Width A of Absorbent core | 23.8 | 10 | 15 | 35 | 50 | 23.8 |
| Width B of Absorbent core | 23.8 | 10 | 15 | 35 | 50 | 23.8 |
| Side slit width | 7.5 | 7.5 | 7.5 | 7.5 | 7.5 | 3 |
| Center slit width | 10 | 10 | 10 | 10 | 10 | 5 |
| Total width of absorbent body | 120.2 | 65 | 85 | 165 | 225 | 106.2 |
| Wearing feeling/W-letter shape | ○ | ○ to Δ | ○ to Δ | ○ to Δ | X | ○ to Δ |

Unit: mm
○: Good
Δ: Acceptable
X: Poor

Second Example

A second example uses the same disposable diaper 1 as that of the first example except for that the disposable diaper 1 of the first example is structured so that the lateral low rigidity section has a width of 10 mm and the center low rigidity section has a width of 10 mm. Thus, the absorbent body 4 had a total width of 65 mm.

Third Example

A third example uses the same disposable diaper 1 as that of the first example except for that the disposable diaper 1 of the third example is structured so that the lateral low rigidity section has a width of 15 mm and the center low rigidity section has a width of 15 mm. Thus, the absorbent body 4 had a total width of 85 mm.

Fourth Example

A fourth example uses the same disposable diaper 1 as that of the first example except for that the disposable diaper 1 of the fourth example is structured so that the lateral low rigidity section has a width of 35 mm and the center low rigidity section has a width of 35 mm. Thus, the absorbent body 4 had a total width of 165 mm.

First Comparative Example

A first comparative example uses the same disposable diaper 1 as that of the first example except for that the disposable diaper 1 of the first comparative example is structured so that the lateral low rigidity section has a width of 50 mm and the center low rigidity section has a width of 50 mm. Thus, the absorbent body 4 had a total width of 225 mm.

Fifth Example

A fifth example uses the same widths of the side region 34 and the center region 33 as those of the first example but is different in that the lateral low rigidity section 36 has a width of 3 mm and the center low rigidity section 35 has a width of 5 mm. Thus, the absorbent body 4 had a total width of 106.2 mm.

Evaluation

In the case of the first comparative example, the side region 34 and the center region 33 had an excessively-wide width to cause a wide total width of the absorbent body 4 to prevent the diaper from suiting the lateral width of the user's crotch portion. The cross section showed no W-letter shape. In the case of the third example and the fourth example, a slightly improved result was obtained. In the case of the second example, undesirable result was sometimes obtained. Although the widths of the side region 34 and the center region 33 in a range from 15 mm to 35 mm can provide a W-letter shape, it was found that a favorable W-letter shape could be obtained when the widths of the side region 34 and the center region 33 were within a range of about 20 mm to about 25 mm. In the case of the first example in which the side region 34 and the center region 33 had a width of 23.8 mm, the wearing feeling and the W-letter shape were both favorable. With regards to the width of the entire absorbent body, a width of 65 mm or less as shown in the second example is not sufficient to provide a W-letter shape at the crotch region of the user. A width of 200 mm or more on the other hand significantly exceeds the lateral width of the crotch of the user and thus cannot form a desired bent shape. A width from about 80 mm to about 180 mm could provide a clear W-letter shape.

First Example

The disposable diaper according to the first example was prepared so that one edge has a curved shape so as to suit the shape of a user's the leg as shown in FIG. 9 and FIG. 10 and the oblong stretch sheet 11 having a shorter length in the longitudinal direction than that of the back sheet 6 of the disposable diaper 1 by 46% was used to prepare the disposable diaper according to the second embodiment. Specifically, the length of the back sheet 6 is 480 mm and the stretch sheet 11 is 260 mm. A nonwoven cloth was used that was composed of fibers of polyurethane having a basis weight of 14 $g/m^2$ to 30 $g/m^2$ and polypropylene having a basis weight of 17.5 $g/m^2$ to 36 $g/m^2$, and a ratio between polypropylene and polyurethane was 40:60 to 50:50. A stretch sheet 11 is applied being stretched to 180% to the longitudinal direction, having a length of 260 mm.

The above stretch sheet was adhered, by a hot melt adhesive agent, between the back sheet 6 that was mainly composed of polyolefin-base resin and that was composed of a resin film having a basis weight in a range of 10 $g/m^2$ to 30 $g/m^2$ and a side sheet of the leakage preventing gather that was composed of a water-shedding nonwoven cloth having a basis weight in a range of 10 $g/m^2$ to 30 $g/m^2$ and polyurethane elastic yarn of 470 to 940 detex. The pair of stretch sheets were adhered to be opposed to each other at both side edges of the crotch region of the disposable diaper to have an equal distance to the center line CL that extended in the longitudinal direction to halve the disposable diaper 1 in the width direction.

The stretch sheet 11 of the first example was adhered so that one edge at the inner side in the width direction of the center absorbing section was separated from the other edge at the inner side in the width direction of by a distance of 90 mm.

Second Comparative Example

In the second comparative example, the stretch sheet was adhered between the back sheet and the leakage preventing gather as in the first example embodiment. In the second comparative example, the stretch sheet was adhered so that edges at the inner side in the width direction of a pair of stretch sheets were separated by a distance of 30 mm.

Third Comparative Example

In a third comparative example, the stretch sheet was adhered between the back sheet and the leakage preventing gather as in the first example. In the third comparison example, the stretch sheet was adhered so that edges at the inner side in the width direction of a pair of stretch sheets were separated by a distance of 130 mm.

Evaluation

The resultant disposable diapers of the second and third examples and the second and third comparative examples were attached to a human model that had a crotch width of 40 mm and that was based on a 70 years old woman having an average figure. Then, these disposable diapers were evaluated with regards to the shapes of the cross sections of the crotch regions. In the first example, the cross sections showed a clear W-letter shape. In the case of the second comparative example, a distance between a side edge in the width direction of a pair of stretch sheets and a side edge in the width direction of stretch sheet were too short and failed to provide a W-letter shape. In the case of the third comparative example, the distance between a pair of stretch sheets and the stretch sheet was too long. Thus, although a W-letter shape was formed, a height of a convex section at the center of the W-letter shape protruding to the user's body was excessively high when compared with that of first example. This may cause the user to experience an uncomfortable feeling. When the distance between the inner edge in the width direction of a pair of stretch sheets and the inner edge in the width direction of the stretch sheet was changed, a favorable W-letter shape was found when the distance was in a range of 70 mm to 110 mm.

First Example

As shown in Table 2, by changing a position at which the absorbent body 4 was adhered to the surface of the back sheet 6, the positional relation with the stretch sheet was evaluated. In the case of the first example, there was a distance of 5 mm between the outer edge 5a of the adhesion section 5 of the absorbent body 4 and the inner edge 11a of the stretch sheet 11. The inner ends in the width direction of the pair of adhesion sections 5 were adhered at positions having an interval of about 40 mm therebetween. In Table 2, the term "distance" means a distance between the outer edge 5a of the adhesion section of the absorbent body and the inner edge 11a of the stretch sheet. When the outer edge 5a of the adhesion section 5 of the absorbent body 4 was away from the inner edge 11a of the stretch sheet 11, the distance was represented by a negative value. When the outer edge 5a of the adhesion section 5 of the absorbent body 4 was superposed with the inner edge 11a of the stretch sheet 11, the distance was represented by a positive value.

TABLE 2

|  | Fourth Comparative Example | Fifth Comparative Example | Sixth Example | Seventh Example | First Example | Eighth Example | Ninth Example |
|---|---|---|---|---|---|---|---|
| Distance (mm) | −45 | −35 | −25 | −15 | −5 | +5 | +15 |
| W-letter shape/ wearing feeling | X | X | Δ | ○ | ○ | ○ | Δ |

○: Good and unstable shape
Δ: Acceptable
X: Poor and unstable shape

Sixth example

A sixth example is the same as the first example except that a distance of 25 mm was provided between the outer edge 5a of the adhesion section 5 of the absorbent body 4 and the inner edge 11a of the stretch sheet 11.

Seventh Example

A seventh example is the same as the first example except that a distance of 15 mm was provided between the outer edge 5a of the adhesion section 5 of the absorbent body 4 and the inner edge 11a of the stretch sheet 11.

Eighth Example

An eighth example is the same as the first example except that the outer edge 5a of the adhesion section 5 of the absorbent body 4 was superposed on the inner edge 11a of the stretch sheet 11 by 5 mm.

Ninth Example

A ninth example is the same as the first example except for that the outer edge 5a of the adhesion section 5 of the absorbent body 4 was superposed on the inner edge 11a of the stretch sheet 11 by 15 mm.

Fourth Comparative Example

A fourth comparative example is the same as the first example except for that the outer edge 5a of the adhesion section 5 of the absorbent body 4 was separated the inner edge 11a of the stretch sheet 11 by 45 mm.

Fifth Comparative Example

A fifth comparative example is the same as first example except for that the outer edge 5a of the adhesion section 5 of the absorbent body 4 was separated the inner edge 11a of the stretch sheet 11 by 35 mm.

Evaluation

In the case of the fourth and fifth comparative examples, the outer edge 5a of the adhesion section 5 of the absorbent body 4 was excessively separated from the inner edge 11a of the stretch sheet 11 to cause poor shape stability. In the case of the sixth example, the outer edge 5a of the adhesion section 5 of the absorbent body 4 was separated from the inner edge 11a of the stretch sheet 11 by a distance of 25 mm. In the case of the ninth example, the outer edge 5a of the adhesion section 5 of the absorbent body 4 was superposed on the inner edge 11a of the stretch sheet 11 by 15 mm. The sixth and ninth examples showed a slightly stable shape. The first, seventh and eighth examples showed favorable shape stability. In conclusion, the outer edge 5a of the adhesion section 5 of the absorbent body 4 is preferably superposed on the inner edge 11a of the stretch sheet 11 preferably by about 5 mm or the outer edge 5a is preferably separated from the inner edge 11a by about 15 mm. The distance between the outer edge 5a and the inner edge 11a by about 5 mm of the first example was found to be more preferable.

4. The Respective Constituting Members

The following section will describe the respective constituting members of a disposable diaper.

4.1. Chassis

The chassis 2 constitutes the outer shape of the disposable diaper 1. The chassis 2 may be provided by one sheet-like member or may be provided by adhering a plurality of sheet-like members. It is noted that the disposable diaper 1 in this embodiment includes the stretchable chassis 2 having the front torso surrounding region 21 and the rear torso surrounding region 22 and the unstretching crotch region 23 positioned between the front torso surrounding region 21 and the rear torso surrounding region 22. The chassis 2 and the crotch region 23 in the longitudinal direction are joined with the top sheet 3, the absorbent body 4, and the back sheet 6. However, the present invention is not limited to this so long as the diaper is structured so that a sheet in the crotch region facing a not-skin-contacting face from the absorbent body has higher initial tensile strength than that of a sheet on a skin-contacting face. For example, another structure also may be used in which the front torso surrounding region 21 of the chassis 2 is continued from the crotch region 23 positioned between the rear torso surrounding region 22 and the front torso surrounding region 21 and the rear torso surrounding region 22 and only the crotch region is the unstretching one.

The chassis 2 is preferably made of material that is breathable, that has strength to prevent the diaper from being damaged even when the diaper worn by a user receives a load due to compression, distortion, or friction for example, and that does not stimulate the user's skin for example. The material may be a breathable sheet-like member (e.g., nonwoven cloth, perforated plastic sheet).

4.2. Top Sheet

When the diaper is worn by a user, the top sheet 3 as a skin-contacting sheet faces the user's body and is abutted with an excretory part. The top sheet 3 may be entirely or partially liquid-permeable. Alternatively, the top sheet 3 may be composed of one sheet-like member or may be composed of a plurality of sheet-like members.

The top sheet 3 is preferably made of material that has strength to prevent the diaper from being damaged even when the diaper worn by a user receives a load due to compression, distortion, or friction for example and that does not stimulate the user's skin. For example, the material may be a liquid-permeable sheet-like member such as a woven cloth, a non-woven cloth, or a perforated plastic sheet.

4.3. Absorbent Body

The absorbent body 4 absorbs and retains discharged body fluid such as urine. The absorbent body 4 may have a structure obtained by mixing highly absorbing polymer with a hydrophilic fiber to layer the material or a structure in which highly absorbing polymer is fixed to a hydrophilic sheet by hot melt adhesive agent for example. The highly absorbing polymer may be, for example, the one including 80% or more absorbability polymer (e.g., polyacrylate-base one, starch/acrylate-base one) having a water absorption factor of 20 g/g or more and a grain size of 100 to 800 µm.

4.4. Back Sheet

The back sheet 6 may be, for example, a thermoplastic film mainly including polyethylene (PE), polypropylene (PP) or the like, a breathable resin film, a sheet obtained by joining a nonwoven cloth based on the spun bond or the spun lace method or the like with a breathable resin film, or a plurality of layers based on SMS(spun bond, melt blow, and spun bond) for example. Preferably, the back sheet 6 is a resin film mainly including polyolefin-base resin with a basis weight of 10 $g/m^2$ to 30 $g/m^2$ for example.

The back sheet 6 may be obtained by joining the not-skin-contacting face of this back sheet 6 with a nonwoven cloth or the like. The not-skin-contacting face of the back sheet 6 joined with a nonwoven cloth or the like is preferable because it provides an improved touch to a user's skin at the wearing stage for example. When the back sheet 6 is a film, the film may be preferably joined with a nonwoven cloth or the like because it can prevent uncomfortable noise due to fiction of the film for example.

4.5. Elastic Member and Stretch Sheet

An elastic member may be composed of, for example, natural rubber or synthetic rubber (e.g., styrene-butadiene, butadiene, isoprene). The sheet-like elastic member 26 can be formed by a nonwoven cloth of foamed polyurethane having a basis weight of 30 $g/m^2$ to 80 $g/m^2$ or mixed fiber of polyurethane of basis weight of 20 $g/m^2$ to 70 $g/m^2$ and polypropylene for example.

4.6. Adhesive Agent

The top sheet 3 and the absorbent body 4 are adhered to the chassis 2 by hot melt adhesive agent. The top sheet 3 is adhered to the absorbent body 4 by hot melt adhesive agent. It is noted that the joint is not limited to the above hot melt adhesion and also may use, for example, a combination of heat sealing and ultrasonic sealing for example.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An absorbent article having a width and a length orthogonal to the width, comprising:
    a chassis having at least a front torso surrounding region and a rear torso surrounding region arranged along a longitudinal direction of the absorbent article;
    a crotch region provided between the front torso surrounding region and the tear torso surrounding region of the chassis;
    an oblong absorbent body extending from the front torso surrounding region to the rear torso surrounding region along the longitudinal direction, the absorbent body comprising an absorbent core covered with a cover sheet;
    a pair of stretchable sheets arranged at both side edges of outer sides in the width direction of the cover sheet and extending in the longitudinal direction, an outer edge of each of the stretchable sheets being formed to have an arch portion that recesses toward a center line of the absorbent body at a center portion in the longitudinal direction of the stretchable sheets;
    a torso opening section formed at one side when in a wearing mode;
    a pair of leg openings formed at another side when in the wearing mode;
    a skin-contacting face facing an inner face when in the wearing mode;
    a not-skin-contacting face facing an outer face when in the wearing mode; and
    an elastic member arranged along a side edge extending in the longitudinal direction of the crotch region constituting the leg opening,
    wherein the absorbent core includes:
    a first narrow width section;
    a second narrow width section arranged longitudinally spaced from the first narrow width section;
    a center low rigidity section formed along a center line that halves the absorbent article in the width direction; and
    a pair of lateral low rigidity sections provided at both sides of the center low rigidity section in the width direction with a substantially equal interval; wherein
    the crotch region is structured so that the skin-contacting face of the absorbent body has a skin contacting face-side sheet and the not-skin-contacting face has either one of a not-skin contacting face-side sheet and the chassis, and
    wherein a portion of the stretchable sheet that has a narrowest width at the arch portion extends over outer side edge of the cover sheet, and
    the skin contacting face-side sheet has, while in a stretched state, a lower initial tensile strength in the width direction than that of the not-skin contacting face-side sheet or the chassis so that the skin contacting face-side sheet is more easily stretchable in the width direction than the not-skin contacting face-side sheet or the chassis.

2. The absorbent article according to claim 1, wherein the absorbent core further comprises a center absorbing section provided in the longitudinal direction between the first narrow width section and the second narrow width section, and the center absorbing section is shaped so that both edges in the width direction protrude more than the first narrow width section and the second narrow width section protrude to outer sides of the width direction, respectively.

3. The absorbent article according to claim 2, wherein the respective stretchable sheets are arranged to extend over both ends of the center absorbing section in the longitudinal direction to outer sides in the longitudinal direction.

4. The absorbent article according to claim 3, further comprising a pair of side regions arranged widthwise outside each of the pair of lateral low rigidity sections
and a pair of center regions arranged between the center low rigidity section and each of the pair of lateral low rigidity sections, the stretchable sheet is provided to be superposed on the side region in the width direction.

5. The absorbent article according to claim 4, wherein
in the wearing mode of the absorbent article,
the side region is bent so that an end of an outer side in the width direction of the side region is raised in the thickness direction of the absorbent body, and
the center region is bent so that an end of an inner side in the width direction of the center region is raised in the thickness direction,
the absorbent body is consequently deformed to have a W-letter shaped cross section in the width direction of the center absorbing section.

* * * * *